United States Patent [19]
Balkovec et al.

[11] Patent Number: 5,516,756
[45] Date of Patent: May 14, 1996

[54] AZA CYCLOHEXAPEPTIDE COMPOUNDS

[75] Inventors: James M. Balkovec, North Plainfield; Frances A. Bouffard, Scotch Plains; James F. Dropinski, Piscataway, all of N.J.

[73] Assignee: Merck & Co., Inc., Rahway, N.J.

[21] Appl. No.: 333,574

[22] Filed: Oct. 31, 1994

[51] Int. Cl.$^6$ .............................. A61K 38/12; C07K 7/52
[52] U.S. Cl. ..................... 514/11; 514/9; 514/2; 530/317; 530/318; 530/321; 930/270; 930/DIG. 548; 930/DIG. 546
[58] Field of Search .................. 514/11, 9, 2; 530/317, 530/321, 318; 930/270, DIG. 548, DIG. 546

[56] References Cited

U.S. PATENT DOCUMENTS

| | | | |
|---|---|---|---|
| 5,166,135 | 11/1992 | Schmatz | 514/11 |
| 5,194,377 | 3/1993 | Schwartz et al. | 435/71.1 |
| 5,202,309 | 4/1993 | Schwartz et al. | 514/11 |
| 5,378,804 | 1/1995 | Balkovec et al. | 530/317 |

FOREIGN PATENT DOCUMENTS

| | | |
|---|---|---|
| 851310 | 8/1977 | Belgium . |
| 0431350 | 6/1991 | European Pat. Off. . |
| 0462531 | 12/1991 | European Pat. Off. . |
| 0486011 | 5/1992 | European Pat. Off. . |
| 0561639A1 | 9/1993 | European Pat. Off. . |
| 2365554 | 4/1978 | France . |

OTHER PUBLICATIONS

Zanblas, Journal of Medicinal Chemistry, vol. 35, pp. 2843–2855 (1992).
Walzer, . . . "Pneumocystis Carinii—New Clinical Spectrum . . . " NEJM; 324, No. 4, pp. 263–265, Jan. 24, 1991.
Bartlett, et al.,, . . . "Pneumocystis Carinii, An Opportunist . . . " Clinical Microbiology Reviews; 4, No. 2, pp. 137–149, Apr. 1991.
Schwartz, et al., J. Antibiotics; 45 No. 12, pp. 1853–1866 (1992).
Walzer, et al., Diagn. Microbiol. Infect. Dis.; 21, pp. 1–6, 1984.

*Primary Examiner*—Christina Y. Chan
*Assistant Examiner*—T. D. Wessendorf
*Attorney, Agent, or Firm*—Elliott Korsen; Mark R. Daniel

[57] ABSTRACT

The present invention is directed to novel aza cyclohexapeptide compounds of the formula

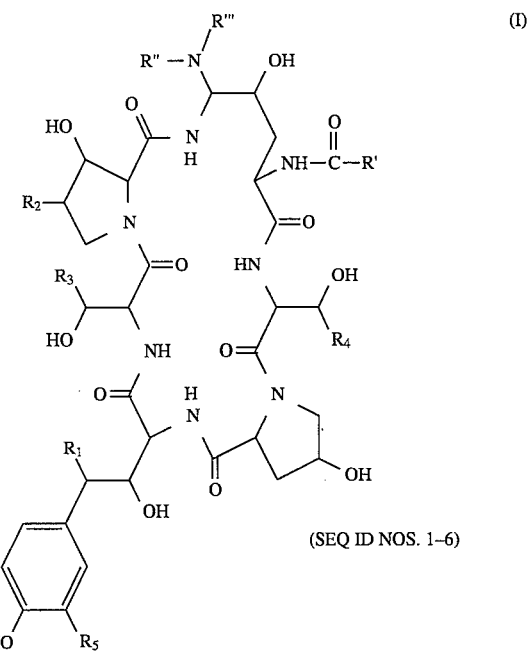

(SEQ ID NOS. 1–6)

where all substituents are defined herein, which are useful as antifungal agents and for the treatment of *Pneumocystis carinii* infections. Compositions containing the compounds of the invention are also disclosed.

5 Claims, No Drawings

AZA CYCLOHEXAPEPTIDE COMPOUNDS

BACKGROUND OF THE INVENTION

The present invention is directed to certain aza cyclohexapeptide compounds which are useful as antifungal and anti-Pneumocystis agents.

There presently exists a need for antifungal and anti-Pneumocystis agents due to an increase in the number of isolates which are resistant to conventional agents. Additionally, conventional agents show somewhat high levels of toxicity which limit their usefulness. Lastly, the incidence of *Pneumocystis carinii* pneumonia is increasing, particularly in view of the high incidence of immuno-compromised patients susceptible to infection, such as those suffering from AIDS.

SUMMARY OF THE INVENTION

The compounds of the present invention, Compound I (Seq. ID Nos. 1–6), are characterized in having an amine or amine derivative attached to the cyclohexapeptide ting at the 5-carbon of the 4-hydroxyomithine component (hereinafter "C-5-orn") and may be represented by the formula:

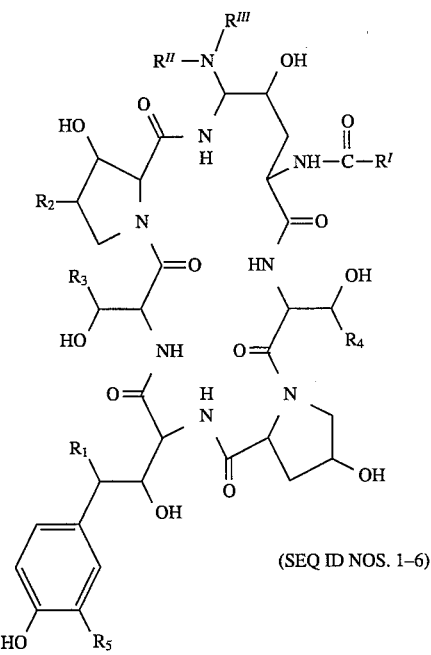

(SEQ ID NOS. 1–6)

(I)

wherein $R_1$ is H or OH;

$R_2$ is H, $CH_3$ or OH:

$R_3$ is H, $CH_3$, $CH_2CONH_2$, $CH_2CN$, $CH_2CH_2NH_2$, $CH_2CH_2N(R^{IV})_3{}^+X^-$ or $CH_2CH_2NH(C=NH)R^{VII}$;

$R_4$ is H or $CH_3$;

$R_5$ is H, OH or $OSO_3H$;

$R^I$ is $C_9$–$C_{21}$ alkyl, $C_9$–$C_{21}$ alkenyl, $C_1$–$C_{10}$ alkoxyphenyl, $C_1$–$C_{10}$ alkoxynaphthyl, or

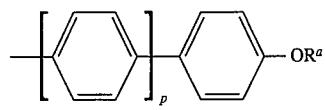

wherein $R^a$ is $C_1$–$C_{10}$ alkyl; or $(CH_2)_q NR^b R^c$ wherein $R^b$ and $R^c$ are independently H, $C_1$–$C_{10}$ alkyl or $R^b$ and $R^c$ taken together with the nitrogen atom are

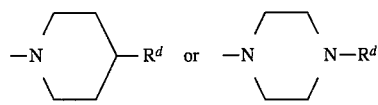

wherein $R^d$ is $C_1$–$C_{16}$ alkyl, cyclohexylmethyl, phenyl or benzyl;

p is 1 or 2;

q is 2, 3 or 4;

$R^{II}$ is $COCH(NR^V R^{VI})(CH_2)_{1-4}NR^V R^{VI}$, $(CH_2)_{2-4}N(R^{IV})_3{}^+X^-$, $(CH_2)_{2-4}NH(C=NH)R^{VII}$ $(CH_2)_{1-4}CH(NR^V R^{VI})(CH_2)_{1-4}NR^V R^{VI}$, $(CH_2)_{2-4}NR^V(CH_2)_{2-4}NR^V R^{VI}$ or $(CH_2)_{2-4}NR^V(CH_2)_{2-4}NR^V(CH_2)_{2-4}NR^V R^{VI}$;

$R^{III}$ is H or $C_1$–$C_4$ alkyl;

$R^{IV}$ is $C_1$–$C_4$ alkyl;

$R^V$ is H or $C_1$–$C_4$ alkyl;

$R^{VI}$ is H or $C_1$–$C_4$ alkyl;

$R^{VII}$ is H, $C_1$–$C_4$ alkyl or $NH_2$;

X is Cl, Br or I; or a pharmaceutically acceptable acid addition salt thereof.

Additionally, there are disclosed quaternary ammonium salts of the formula

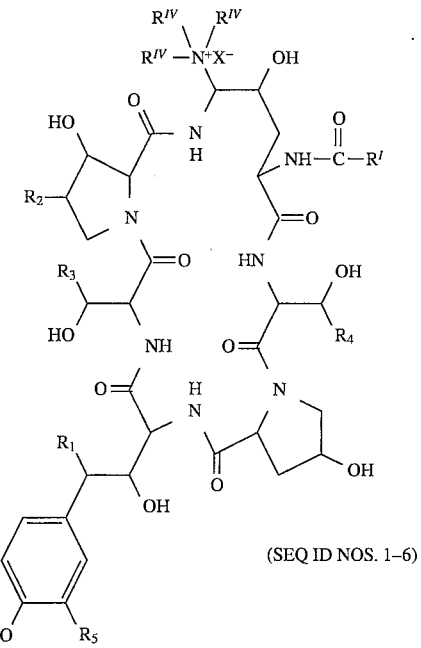

(SEQ ID NOS. 1–6)

(II)

where $R_1$, $R_2$, $R_3$, $R_4$, $R_5$, $R^I$, $R^{IV}$ and X are as defined above.

There are also disclosed compounds of the formula

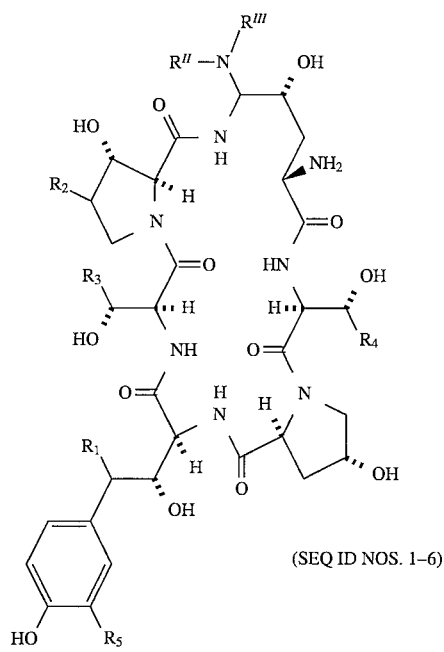

(SEQ ID NOS. 1–6)

wherein $R_1$ is H or OH;

$R_2$ is H, $CH_3$ or OH;

$R_3$ is H, $CH_3$, $CH_2CONH_2$, $CH_2CN$, $CH_2CH_2NH_2$, $CH_2CH_2N(R^{IV})_2{}^+X^-$ or $CH_2CH_2NH(C=NH)R^{VII}$;

$R_4$ is H or $CH_3$;

$R_5$ is H, OH or $OSO_3H$;

$R^{II}$ is $COCH(NR^VR^{VI})(CH_2)_{1-4}NR^VR^{VI}$, $(CH_2)_{2-4}N(R^{IV})_3{}^+X^-$, $(CH_2)_{2-4}NH(C=NH)R^{VII}$ $(CH_2)_{1-4}CH(NR^VR^{VI})(CH_2)_{1-4}NR^VR^{VI}$, $(CH_2)_{2-4}NR^V(CH_2)_{2-4}NR^VR^{VI}$ or $(CH_2)_{2-4}NR^V(CH_2)_{2-4}NR^V(CH_2)_{2-4}NR^VR^{VI}$;

$R^{III}$ is H or $C_1$–$C_4$ alkyl;

$R^{IV}$ is $C_1$–$C_4$ alkyl;

$R^V$ is H or $C_1$–$C_4$ alkyl;

$R^{VI}$ is H or $C_1$–$C_4$ alkyl;

$R^{VII}$ is H, $C_1$–$C_4$ alkyl or $NH_2$;

X is Cl, Br or I; or a pharmaceutically acceptable acid addition salt thereof, which are useful for the preparation of Compounds I and II of the invention.

Preferred embodiments of the invention are those of Compound I wherein $R_1$ is OH, $R_2$ is H, $R_3$ is $CH_2CH_2NH_2$, $R_4$ is $CH_3$, $R_5$ is H, $R^I$ is dimethyltridecyl and $NR''R'''$ is

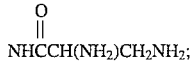

or where $R_1$ is OH, $R_2$ is H, $R_3$ is $CH_2CH_2NH_2$, $R_4$ is $CH_3$, $R_5$ is H, $R^I$ is 6-octyloxy-2-naphthyl, and $NR''R'''$ is

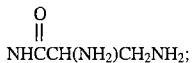

or where $R_1$ is OH, $R_2$ is H, $R_3$ is $CH_2CH_2NH_2$, $R_4$ is $CH_3$, $R_5$ is H, $R^I$ is dimethyltridecyl and $NR''R'''$ is $HN(CH_2)_2NH(CH_2)_2NH_2$;

or where $R_1$ is OH, $R_2$ is H, $R_3$ is $CH_2CH_2NH_2$, $R_4$ is $CH_3$, $R_5$ is H, $R^I$ is

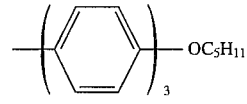

or of Compound II where $R_1$ is OH, $R_2$ is H, $R_3$ is $CH_2CH_2NH_2$, $R_4$ is $CH_3$, $R_5$ is H, $R^I$ is dimethyltridecyl, and $N(R^{IV})_3{}^+X^-$ is $N(CH_3)_3{}^+I^-$.

The compounds of this invention may be formulated into pharmaceutical compositions which are comprised of the compounds of formula I in combination with a pharmaceutically acceptable carrier.

The compounds of this invention are useful in treating fungal infections and for the treatment and prevention of infections caused by *Pneumocystis carinii*. These infections are often found in immunocomprised patients such as those suffering with AIDS.

Throughout the specification and appended claims, a given chemical formula or name shall encompass all optical and stereoisomers as well as racemic mixtures where such isomers and mixtures exist.

The term alkyl refers to straight, branched or cyclic chain hydrocarbon groups, e.g., methyl, ethyl, n-propyl, isopropyl, n-butyl, pentyl, hexyl, heptyl, cyclopentyl, cyclohexyl, cyclohexylmethyl and the like.

The term cycloalkyl refers to a species of alkyl containing from 3 to 15 carbon atoms without alternating or resonating double bonds between carbon atoms.

The term alkenyl refers to groups such as, e.g., vinyl, 1-propene-2-yl, 1-butene-4-yl, 2-buten-4-yl, 1-pentene-5-yl and the like.

The term alkoxy refer to straight or branched chain oxyalkyl groups such as, e.g., methoxy, ethoxy, butoxy, heptoxy, dodecyloxy, and the like.

The compounds of the present invention are generally obtained as mixtures of stereoisomeric forms in which one form usually s predominates. Conditions may be adjusted by means within the normal skill of the skilled artisan to obtain predominantly the desired isomer. The compounds with preferred stereoisomeric form designated herein as the "normal" form are those in which the group at the "C-5-orn" position is below the plane at the said position. The designation "epi" has been employed for those compounds in which the group at the "C-5-orn" position is above the plane.

Pharmaceutically acceptable salts suitable as acid addition salts are those from acids such as hydrochloric, hydrobromic, phosphoric, sulfuric, maleic, citric, acetic, tartaric, succinic, oxalic, malic, glutamic and the like, and include other acids related to the pharmaceutically acceptable salts listed in *Journal of Pharmaceutical Science*, 66:2 (1977).

When the acyl substituent at the 2-position on the 4-hydroxyornithine nitrogen contains an aromatic chain, it differs from natural products and known compounds. The aromatic chain disclosed is one of at least two phenyl groups further extended by substituents in the para position.

Representative nuclei for the aza derivatives of the present invention (Compounds I & H) and the sequence ID for these compounds may be seen in the following table. Since the peptide nuclei would be the same irrespective of substituents $R^I$, $R^{II}$, or $R^{III}$ and since the sequence identification number is assigned for the nuclear variations, the amines and salts have the same sequence ID's.

| Aza Compound | $R_3$ | $R_4$ | SEQ ID NO. |
|---|---|---|---|
| I-1 | H | $CH_3$ | 1 |
| I-2 | $CH_3$ | $CH_3$ | 2 |
| I-3 | All Others | $CH_3$ | 3 |
| I-4 | H | H | 4 |
| I-5 | $CH_3$ | H | 5 |
| I-6 | All Others | H | 6 |

The compounds are soluble in lower alcohols, and polar aprotic solvents such as N,N-dimethylformamide (DMF), dimethyl sulfoxide (DMSO) and pyridine. They are insoluble in solvents such as diethyl ether and acetonitrile.

The compounds of the present invention are useful as an antibiotic, especially as an antifungal agent or as an antiprotozoal agent. As antifungal agents they are useful for the control of both filamentous fungi and yeasts. They are especially adaptable to be employed for the treatment of mycotic infections in mammals, especially those caused by Candida species such as *C. albicans*, *C. tropicalis* and *C. pseudotropicalis*, Cryptococcus species such as *C. neoformans* and Aspergillus species such as *A. fumigatus*, *A. flavus*, *A. niger*. They are also useful for the treatment and/or prevention of *Pneumocystis carinii* pneumonia to which immune-compromised patients are especially susceptible as hereinafter described.

The structural aspects which distinguish the compounds of the present invention are the amine or amine derivative attached to the cyclohexapeptide ring at the 5-carbon of the 4-hydroxyornithine residue. For the desirable combination of properties, the amino acids of the nucleus are not changed.

The compounds of the present invention may be prepared from cyclopeptides having the formula

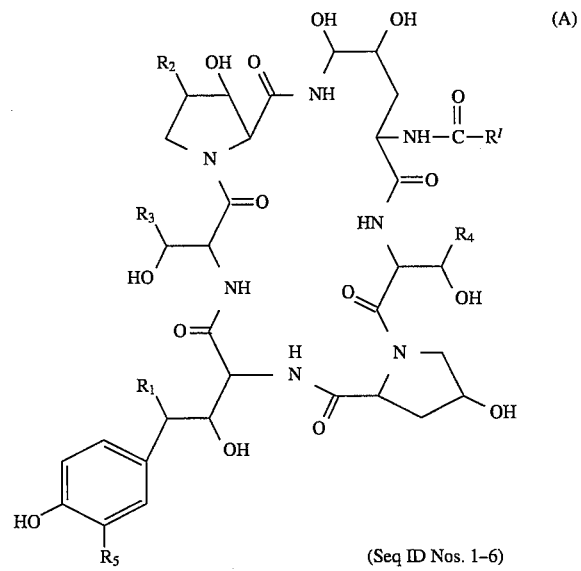

(Seq ID Nos. 1–6)

by a series of reactions in which the oxygen atom at the "C-5-orn" (which also may be referred to as the hemiaminal position) is ultimately replaced by nitrogen. The starting materials may be natural products or modified natural products as subsequently described. When $R_1$ is hydrogen instead of hydroxyl, the product aza compounds may be prepared by an alternate series of reactions.

The sequence IDs of the starting materials are seen in the following table:

| Compound | $R_3$ | $R_4$ | Starting Material SEQ ID NO. |
|---|---|---|---|
| A-1 | H | $CH_3$ | 7 |
| A-2 | $CH_3$ | $CH_3$ | 8 |
| A-3 | AU Others | $CH_3$ | 9 |
| A-4 | H | H | 10 |
| A-5 | $CH_3$ | H | 11 |
| A-6 | All Others | H | 12 |

A compound where $R_1$ is OH, $R_2$ is H, $R^I$ is dimethyltridecyl has been identified in the literature as pneumocandin $B_o$ and a compound where $R_1$ is OH, $R_2$ is $CH_3$, $R_3$ is $CH_2CONH_2$ and $R^1$ is dimethyltridecyl has been identified as pneumocandin $A_o$ (J. Antibiotics 45:1855–60, Dec. 1992). A compound where $R_1$ and $R_2$ are OH and $R^I$ is dimethyltridecyl has been identified as pneumocandin $D_o$ (J. Antibiotics 47:755–764, July 1994).

When in the starting compound, $R_1$ and $R_2$ are represented by any of the possible variables and $R_3$ is H, $CH_3$ or $CH_2CONH_2$, they may be directly employed in the first method shown. When $R_3$ is $CH_2CN$, $CH_2CH_2NH_2$, $CH_2CH_2N(R^{IV})_3{}^+X^-$ or $CH_2CH_2NH(C=NH)R^{VII}$, the amides must be first converted to $CH_2CN$ or $CH_2CH_2NH_2$ and then modified, to be reacted in the first method. Alternatively, a compound in which $R_3$ is $CH_2CONH_2$ may be employed s to produce a compound with N at the hemiaminal position, and the $CH_2CONH_2$ of the resulting product then converted to $CH_2CN$ or $CH_2CH_2NH_2$.

First, when $R_1$, $R_2$ and $R_3$ of the starting material are the same as those in the product, the following reaction steps may be employed:

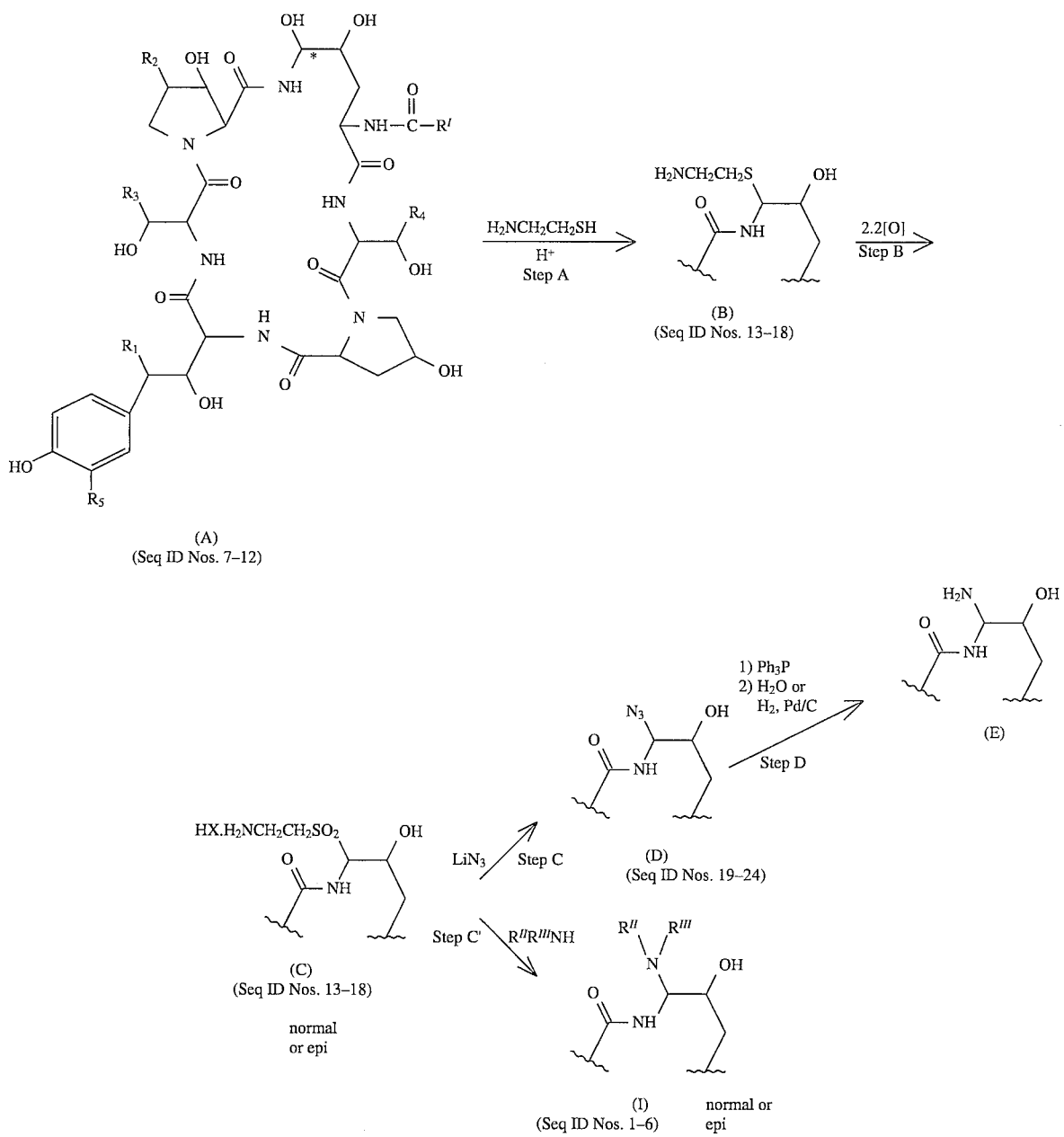

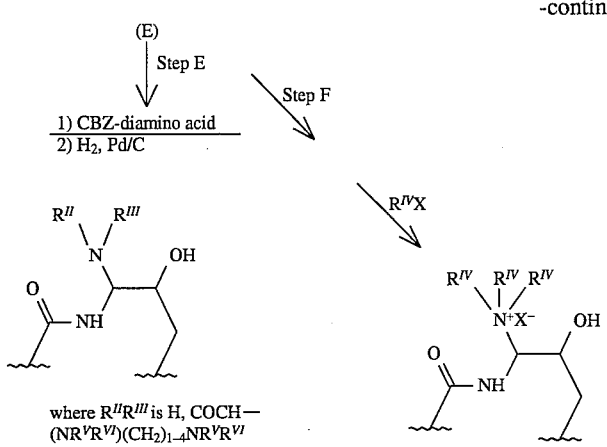

where $R^{II}R^{III}$ is H, COCH—
$(NR^VR^{VI})(CH_2)_{1-4}NR^VR^{VI}$

* The position is the "C-5-orn" or the hemiaminal position.

In Step A, the starting material Compound A (Seq ID Nos. 7–12), alkylthiol or arylthiol and acid are caused to react in an aprotic solvent under anhydrous conditions for time sufficient for reaction to take place with the formation of Compound B (Seq ID Nos. 13–18), seen in the following table. Aminoethanethiol has been found to be useful for this step.

| Compound | $R_3$ | $R_4$ | Sulfur Intermediate SEQ ID NO. |
|---|---|---|---|
| B-1 | H | $CH_3$ | 13 |
| B-2 | $CH_3$ | $CH_3$ | 14 |
| B-3 | All Others | $CH_3$ | 15 |
| B-4 | H | H | 16 |
| B-5 | $CH_3$ | H | 17 |
| B-6 | All Others | H | 18 |

For Step A, suitable acids include strong organic acid and mineral acids. Examples of strong organic acids are camphorsulfonic acid, p-toluenesulfonic acid, trifluoroacetic acid and methanesulfonic acid. Mineral acids include hydrochloric acid and hydrobromic acid. Camphorsulfonic acid is preferred.

Suitable solvents include DMF, DMSO, 1-methyl-2-pyrrolidinone and hexamethyl phosphoric triamide (HMPA). DMF or DMSO is preferred.

The reaction is generally carded out at ambient temperature to 60° C. for about 3 hours to about 10 days.

In carrying out the reaction, the cyclohexapeptide compound, the thiol compound and acid are stirred together in a suitable solvent until the reaction is substantially complete. The reaction mixture then is diluted with water and flash chromatographed on reverse phase resins using 10 to 40 percent acetonitrile/water (containing 0.1% trifluoroacetic acid) as eluant. Trifluoroacetic acid may hereinafter be designated "TFA". The fractions containing the desired product may be concentrated and lyophilized and the lyophilized material purified by preparative high performance liquid chromatography (HPLC).

Appropriate columns for HPLC are commercially available columns sold under trade mark names or trade names such as "ZORBAX" (DuPont), "DeltaPak" (Waters), "LICHROPREP" RP 18 (E. Merck). The specific columns are identified in the working examples.

In Step B, Compound C (Seq ID Nos. 13–18), a sulfone is obtained by the oxidation of Compound B. Suitable oxidizing agents or oxidants include "OXONE" $(KHSO_5 \cdot KHSO_4 \cdot K_2SO_4$ 2:1:1, Aldrich Chemicals), metachloroperoxybenzoic acid, and peroxyacetic acid. The sequence ID of Compound C is the same as that of Compound B since the atom attached to the hemiaminal carbon is still sulfur. Thus, the o sequence IDs of the sulfones are as follows:

| Compound | $R_3$ | $R_4$ | Sulfone SEQ ID NO. |
|---|---|---|---|
| C-1 | H | $CH_3$ | 13 |
| C-2 | $CH_3$ | $CH_3$ | 14 |
| C-3 | All Others | $CH_3$ | 15 |
| C-4 | H | H | 16 |
| C-5 | $CH_3$ | H | 17 |
| C-6 | All Others | H | 18 |

The oxidation of the thioether (Compound B) to the sulfone (Compound C) is carded out with about two molar amounts of the oxidant. When one molar amount of oxidant is employed, the product is a sulfoxide which may then be converted to the sulfone. The sulfoxides may be employed as an intermediate in the formation of the aza compounds but the sulfone is preferred. A slight excess over the two molar amount of the oxidizing agent is employed.

The reaction is carded out in an aqueous medium, preferably a mixture of acetonitrile and water. About equal amounts are preferred although a range of 1:9 to 9:1 may be employed.

In carrying out the reaction, the oxidant is added to a solution of Compound B (Seq ID Nos. 13–18) in 1:1 acetonitrile/water and the mixture allowed to stand at ambient temperature for time sufficient to complete the reaction to obtain Compound C generally from about 30 minutes to one hour.

After completion of the reaction, the compound is recovered from the reaction mixture by diluting with water and chromatographing. Reverse phase (C18) flash column chromatography is suitable in this purification step. The preferred eluting agent is 30–45 percent acetonitrile/water (0.1% TFA) in 5 percent step gradients. The appropriate fractions are lyophilized to recover the desired sulfone intermediate, Compound C (Seq ID Nos. 13–18). The intermediate tends to be labile, thus the isolation should be carded out as rapidly as possible. Alteratively, the reaction mixture can be lyophilized and the crude sulfone used as is in the subsequent step.

Compound C may be converted to a compound having a nitrogen directly attached to the "C-5-orn". As seen in the flow diagram, reaction of Compound C with an alkali metal azide produces an azide at that position (Compound D) while reaction with an amine compound produces an amino group at the "C-5-orn" position. Compound D is an important intermediate for most of the compounds of the present invention. Although Compound D has nitrogen at "C-5-orn", since it is not a product, separate sequence ID Nos. are assigned for Compound D. Sequence ID Nos. for Compound D are found in the following table.

| Compound | $R_3$ | $R_4$ | Azide SEQ ID NO. |
|---|---|---|---|
| D-1 | H | $CH_3$ | 19 |
| D-2 | $CH_3$ | $CH_3$ | 20 |
| D-3 | All Others | $CH_3$ | 21 |
| D-4 | H | H | 22 |
| D-5 | $CH_3$ | H | 23 |
| D-6 | All Others | H | 24 |

The azide may be obtained by adding alkali metal azide while stirring at ambient temperature to a solution of the sulfone in an aprotic solvent for time sufficient to complete the reaction with the formation of the azide as determined by HPLC analysis. The reaction mixture then may be diluted with water and then chromatographed to separate the desired azide (Compound D) from the reaction mixture. Reverse-phase (C18) flash column chromatography using 20–60% acetonitrile/water (0.1% TFA) in 10% step gradients is suitable for this procedure.

The azide (Compound D) may then be reduced to a compound having a free amino group (Compound E).

The reduction may be carried out by mixing the azide compound (Compound D) with Pd/C in a solvent such as glacial acetic acid and hydrogenating under balloon pressure for 10 to 20 hours. The product then may be recovered by first removing the catalyst by filtration and the filtrate lyophilized to obtain the amine compound (Compound E) in which the amine is a primary amine.

To selectively prepare derivatives of the C5-orn amine when $R_3$ also contains an amine (i.e., $R_3$=$CH_2CH_2NH_2$), the amino of $R_3$ may first be protected as a CBZ derivative prior to reduction of the azide. The azide is then reduced by treatment with triphenylphosphine in a solvent such as DMF followed by $H_2O$. The mono-CBZ bisamine is isolated by reverse-phase (C18) chromatography using acetonitrile/water containing 0.1% TFA.

The amine thus obtained may be convened into an acylated amine by conventional means using a CBZ protected amino acid to obtain, after deprotection, Compound I where $R''$ is $COCH(NH_2)(CH_2)_{1-4}NH_2$ and $R'''$ is H.

Compound I where $R''$ is not acyl may be prepared directly from the sulfone by a method in which the appropriate amine is caused to react with the sulfone.

The reaction is carded out in an aprotic solvent such as those previously named and at ambient temperature. About tenfold molar excess of the amine compound is employed. The reaction may be carried out over one to several hours.

In carrying out the reaction, the appropriate amine is added to a solution of the sulfone in anhydrous aprotic solvent and the reaction s mixture stirred at ambient temperature to obtain Compound I in which the substituent at "C-5-orn" is $NHR''$. The desired compound may then be recovered by diluting with aqueous acetic acid and then chromatographing. Reverse phase (C18)chromatography eluting with 10 to 25 % acetonitrile/water (0.1% acetic acid) in 5% step gradients is suitable. The appropriate fractions may be lyophilized to recover the product as an acetate salt.

The (trifluoro)acetate salt (Compound I) may be converted by dissolving the salt in water and passing through a Bio-Rad AG2-X8 (Cl⁻) polyprep column and recovering the product as the hydrochloride salt.

When $R_1$ in formula (I) is hydrogen, the nitrogen may be introduced directly into the hemiaminal position by a reaction to form the azide, which then is reduced to an amime which optionally may be alkylated or acylated to obtain the ultimate product. The reaction is seen by the following flow diagram.

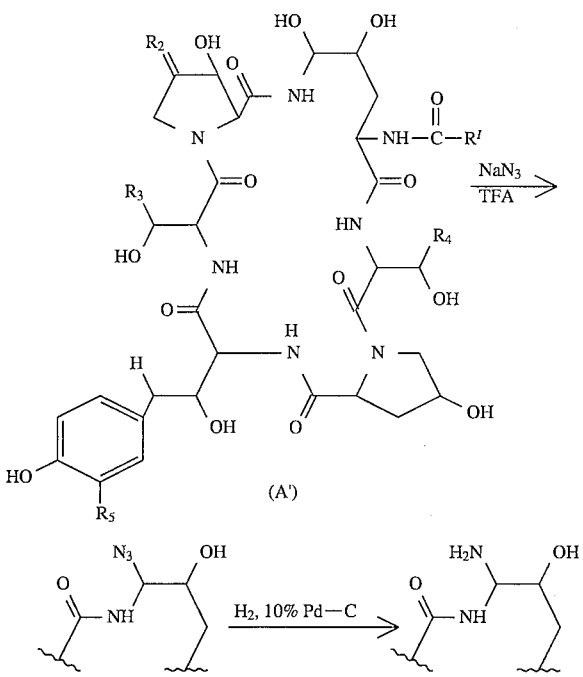

(A')

Although $R_1$ is hydrogen in some natural product cyclohexapeptides, $R_1$ is more commonly hydroxyl. Thus, for a number of the compounds, Compound A' in the flow diagram is prepared as a first step from the corresponding compound in which $R_1$ is OH.

The preparation of the reduced compound may be carded out by stirring the appropriate hydroxy compound in $LiClO_4$-diethyl ether at room temperature, adding trifluoroacetic acid, followed by triethylsilane and subjecting the mixture to rapid stirring for from 4 to 10 hours or until the starting hydroxy compound is no longer detectable by analytical HPLC. The reaction-mixture is then poured into distilled water to obtain the reduced product as precipitate which then is recovered by conventional procedures. The reduced product thus obtained may be used with or without purification in the preparation of the azide.

Products in which $R_1$ is H, may be obtained by adding the modified cyclohexapeptide to a preformed solution of $HN_3$. $HN_3$ may be prepared from sodium azide and trifluoroacetic acid. The reaction is allowed to take place at room temperature to obtain the azide product which may be recovered by conventional procedures and purified by HPLC.

The purified azide compound may be reduced to the amine compound by hydrogenating with palladium/carbon in a manner similar to that previously described.

The invention also embraces quaternary ammonium salts of Compound E and Compound I, where $R''R'''$ does not include an acyl substituent. These may be prepared by treatment of an amine with an alkyl halide and base in a protic or aprotic solvent. A typical procedure would be to add excess methyl iodide to a solution of the amine and sodium bicarbonate in DMF at room temperature. The product may be isolated by diluting with $H_2O$ and C18 HPLC.

The invention also embraces acid addition salts. The compound in the normal course of isolation is obtained as an acid addition salt. Generally, it is as a trifluoroacetic acid or acetic acid salt. The salt thus obtained may be dissolved in water and passed through an anion exchange column bearing the desired anion. The eluate containing the desired salt may be concentrated to recover the salt as a solid product.

The compounds of the present invention are active against many fungi and particularly against Candida species. The antifungal properties may be illustrated with the minimum fungicidal concentration (MFC) determination against certain Candida organisms in a microbroth dilution assay carded out in a Yeast Nitrogen Base (DIFCO) medium with 1% dextrose (YNBD).

In a representative assay, compounds were solubilized in 100% dimethyl sulfoxide (DMSO) at an initial concentration of 5 mg/ml. Once dissolved, the drug stock was brought to a concentration of 512 µg/ml by dilution in water such that the final DMSO concentration was about 10 percent. The solution was then dispensed via a multichannel pipetter into the first column of a 96-well plate (each well containing 0.075 ml of YNBD), resulting in a drug concentration of 256 µg/ml. Compounds in the first column were diluted 2-fold across the rows yielding final drug concentration ranging from 256 µg/ml to 0.12 µg/ml.

Four-hour broth cultures of organisms to be tested were adjusted using a spectrophotometer at 600 nm to equal a 0.5 McFarland Standard. This suspension was diluted 1:100 in YNBD to yield a cell concentration of $1-5 \times 10^4$ colony forming units (CFU)/ml. Aliquots of the suspension (0.075 ml) were inoculated into each well of the microtiter plate resulting in a final cell inoculum of $5-25 \times 10^3$ CFU/ml and final drug concentrations ranging from 128 µg/ml to 0.06 µg/ml. Each assay included one row for drug-free control wells and one row for cell-free control wells.

After 24 hours of incubation, the microtiter plates were shaken gently on a shaker to resuspend the cells. The MIC-2000 inoculator was used to transfer a 1.5 microliter sample from each well of the 96-well microtiter plate to a single reservoir inoculum plate containing Sabouraud dextrose agar (SDA). The inoculated SDA plates were incubated for 24 hours at 35° C. and then read for minimum fungicidal concentration (MFC). MFC is defined as the lowest concentration of drug showing no growth or less than 4 colonies per spot. Compound I ($R_1$=OH, $R_2$=H, $R_3$=$CH_2CH_2NH_2$, $R_4$=$CH_3$, $R'$=dimethyltridecyl and $R''R'''$=CO—(S)—$CH(NH_2)CH_2NH_2$) as its acid addition salt had the following MFCs:

| | |
|---|---|
| Candida albicans (MY 1055) | 1 µg/ml |
| Candida parapsilosis (MY 1010) | 0.5 µg/ml |
| Candida tropicalis (MY 1012) | 1 µg/ml |

The *in vivo* effectiveness of the compounds against fungi may be seen in the following assay.

Growth from an overnight SDA culture of *Candida albicans* MY 1055 was suspended in sterile saline and the cell concentration determined by hemacytometer count and the cell suspension adjusted to $3.75 \times 10^5$ cells/ml. Then 0.2 milliliter of this suspension was administered I.V. in the tail vein of mice so that the final inoculum is $7.5 \times 10^4$ cells/mouse.

The assay was then carried out by administering aqueous solutions of Compound I at various concentrations intraperitoneally (I.P.), twice daily (b.i.d.) for four consecutive days to 18 to 20 gram female DB A/2 mice, which previously had been infected with *Candida albicans* (MY 1055) in the manner described above. Distilled water was administered I.P. to *C. albicans* challenged mice as controls. After seven days, the mice were sacrificed by carbon dioxide gas, paired kidneys were removed aseptically and placed in sterile polyethylene bags containing 5 milliliters of sterile saline. The kidneys were homogenized in the bags, serially diluted in sterile saline and aliquots spread on the surface of SDA plates. The plates were incubated at 35° C. for 48 hours and yeast colonies enumerated for determination of colony forming units (CFU) per gram of kidneys. Compound I with R groups as defined above gave greater than 99% reduction of recoverable Candida CFUs at 0.07 mg/kg i.p. twice daily for four consecutive days.

A harmful and potentially fatal side reaction of a number of drugs including certain antibiotically active echinocandin compounds is red blood cell lysis. This is not seen in compounds having the present nuclei which is another advantage of the compounds of this invention. Additionally, the compounds of this invention are less toxic than certain alkyl side chain hexapeptide analogs.

The compounds of the present invention may also be useful for inhibiting or alleviating *Pneumocystis carinii* infections in immune-compromised patients. The efficacy of the compounds of the present invention for therapeutic or anti-infection purposes may be demonstrated in studies on immunosuppressed rats.

Sprague-Dawley rats (weighing approximately 250 grams) are immunosuppressed with dexamethasone in the drinking water (2.0 mg/L) and maintained on a low protein diet for seven weeks to induce the development of Pneumocystis pneumonia from a latent infection. Before drug treatment, two rats are sacrificed to confirm the presence of *Pneumocystis carinii* pneumonia (PCP). Five rats (weighing approximately 150 grams) are injected twice daily for four days subcutaneously (sc) with Compound in 0.25 ml of vehicle (distilled water). A vehicle control is also carded out. All animals continue to receive dexamethasone in the drinking water and low protein diet during the treatment period. At the completion of the treatment, all animals are sacrificed, the lungs are removed and processed, and the extent of disease determined by microscopic analysis of stained slides. The prevention or reduction of cysts are seen in slides of the lungs of treated rats when compared with the number of cysts in the lungs of untreated controls or solvent controls.

The outstanding properties are most effectively utilized when the compound is formulated into novel pharmaceutical compositions with a pharmaceutically acceptable carder according to the conventional pharmaceutical compounding techniques.

The novel compositions contain at least a therapeutic antifungal or antipneumocystis amount of the active compound. Generally, the composition contains at least 1% by weight of Compound I or II. Concentrate compositions suitable for dilutions prior to use may contain 90% or more by weight. The compositions include compositions suitable for oral, topical, parenteral (including intraperitoneal, subcutaneous, intramuscular, and intravenous), nasal, and suppository administration, or insufflation. The compositions may be prepacked by intimately mixing Compound I or II with the components suitable for the medium desired.

Compositions formulated for oral administration may be a liquid composition or a solid composition. For liquid preparation, the therapeutic agent may be formulated with liquid carders such as water, glycols, oils, alcohols, and the like, and for solid preparations such as capsules and tablets, with solid carriers such as starches, sugars, ethyl cellulose, calcium and sodium carbonate, calcium phosphate, kaolin, talc, lactose, generally with lubricant such as calcium stearate, together with binders disintegrating agents and the like. Because of their ease in administration, tablets and capsules represent the most advantageous oral dosage form. It is especially advantageous to formulate the compositions in unit dosage form (as hereinafter defined) for ease of administration and uniformity of dosage. Compositions in unit dosage form constitute an aspect of the present invention.

Compositions may be formulated for injection and may take such forms as suspensions, solutions or emulsions in oily or aqueous vehicles such as 0.85 percent sodium chloride or 5 percent dextrose in water and may contain formulating agents such as suspending, stabilizing and/or dispersing agents. Buffering agents as well as additives such as saline or glucose may be added to make the solutions isotonic. The compound may also be solubilized in alcohol/propylene glycol or polyethylene glycol for drip intravenous administration. These compositions also may be presented in unit dosage form in ampoules or in multidose containers, preferable with added preservative. Alternatively, the active ingredients may be in powder form for reconstituting with a suitable vehicle prior to administration.

The term "unit dosage form" as used in the specification and claims refers to physically discrete units, each unit containing a predetermined quantity of active ingredient calculated to produce the desired therapeutic effect in association with the pharmaceutical carrier. Examples of such unit dosage forms are tablets, capsules, pills, powder packets, wafers, measured units in ampules or in multidose containers and the like. A unit dosage of the present invention will generally contain from 100 to 200 milligrams of one of the compounds.

When the compound is for antifungal use, any method of administration may be employed. For treating mycotic infections, oral or intravenous administration is usually employed.

When the compound is to be employed for control of Pneumocystis infections it is desirable to directly treat lung and bronchi. For this reason inhalation methods are preferred. For administration by inhalation, the compounds of the present inventions are conveniently delivered in the form of an aerosol spray presentation from pressurized packs or nebulizers. The preferred delivery system for inhalation is a metered dose inhalation (MDI) aerosol, which may be formulated as a suspension or solution of Compound I or II in suitable propellants, such as fluorocarbons or hydrocarbons.

Although the compounds of the present invention may be employed as tablets, capsules, topical compositions, insufflation powders, suppositories and the like, the solubility of the compounds of the present invention in water and aqueous media render them adaptable for use in injectible formulations and also in liquid compositions suitable for aerosol sprays.

The following examples illustrate the invention but are not to be construed as limiting.

EXAMPLE 1

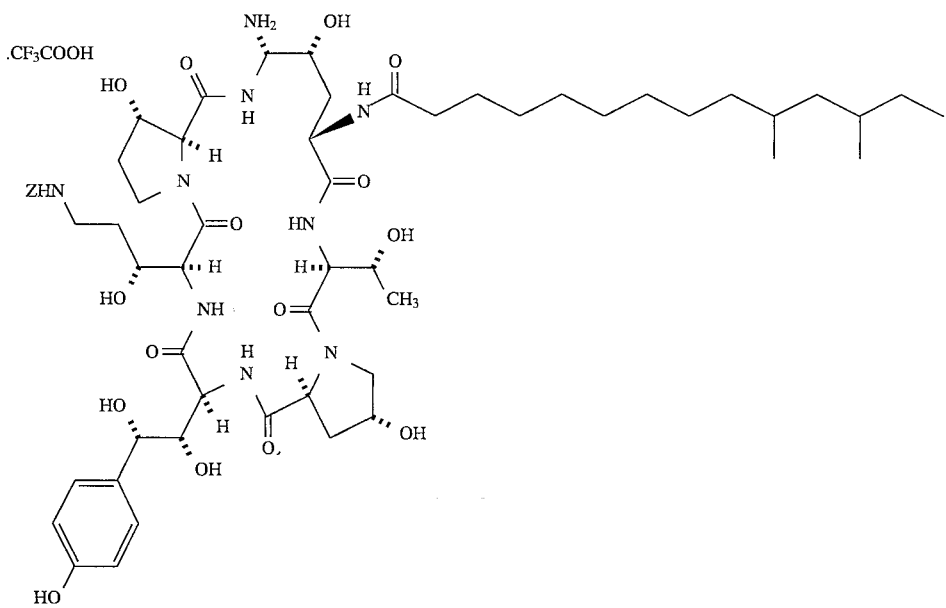

(SEQ ID NO. 3)

Part A: Preparation of Thioether Intermediate

Trifluoracetic acid (0.4 ml, 5.3 mmol) was added to a solution of 22.9 g (21.1 mmol) L-731,373 HCl and 47.9 g (422 mmol) of 2-aminoethanethiol hydrochloride in 100 ml of anhydrous N,N-dimethylformamide at 60° C. After a period of 4 h, the reaction mixture was cooled to room temperature and diluted with 400 ml of $H_2O$. Filtration of the resulting solution was followed by pump-injection of the filtrate onto a Waters Delta Pak C18–100Å radial cartridge (47 mm×30 cm) at a rate of 50 ml/min. Elution with 25–30% $CH_3CN/H_2O$ (0.1% $CF_3COOH$) in one 5% step gradient gave, after lyophilization of the appropriate fractions, 6.5 g of the nor-thioether and 6.8 g of the epi-thioether as bistrifluoracetate salts. By analytical HPLC (Zorbax RXC-18, 40% $CH_3CN/H_2O$ (0.1% $CF_3COOH$) uv at 210 nm), the thioethers were sufficiently pure for conversion to sulfone as described below. Rechromatography of the individual isomers followed by ion exchange on a Bio-Rad AG2-X8 (Cl⁻) column eluting with $H_2O$ provided, after lyophilization, pure bishydrochlorides as amorphous solids. Nor-thioether:

¹H NMR (400 MHz, CD₃OD) δ 1.17 (d, J=6.2 Hz, 3H), 2.9 (m, 2H), 3.06 (t, J=7.2 Hz, 2H), 3.20 (t, J=6.7 Hz, 2H), 4.91 (d, J=5.8 Hz, 2H), 4.99 (d ,J=3.4 Hz), 5.27 (d, J=2.07 Hz, 1H),6.74 (d, J=8.6 Hz, 2H), 7.11 (d, J=8.6 Hz, 2H); FAB-MS (Li) m/z 1117 (MH+ Li)⁺. Epi-thioether: ¹H NMR (400 MHz, CD₃OD) δ 1.17 (d, J=6.2 Hz, 3H), 2.9 (m, 2H), 3.06 (t, J=7.2 Hz, 2H), 3.20 (t, J=6.7 Hz, 2H), 4.91 (d, J=5.8 Hz, 2H), 4.99 (d, J=3.4 Hz), 5.27 (d, J=2.07 Hz, 1H), 6.74 (d, J=8.6 Hz, 2H), 7.11 (d, J=8.6 Hz, 2H); FAB-MS (Li) m/z 1117 (MH+Li)⁺.

Part B: Preparation of epi-Sulfone

To a stirred solution of the epi-thioether from Part A (6.5 g, ~70% pure) in 55 ml of 1:1 acetonitrile/water was added OXONE® (3.1 g). After a period of 15 min., analysis by C18-HPLC showed the conversion to a more polar product to be complete. The reaction was lyophilized to provide the crude sulfone which was used in the subsequent step without purification.

Part C: Preparation of Azide

To a stirred solution of the epi-sulfone bistrifluoroacetate (1.18 g, 0.856 mmol) in 12.5 ml of anhydrous N,N-dimethylformamide was added lithium azide (1.25 g, 25.6 mmol). After a period of 0.5 h, HPLC analysis (RP-C18, 40% CH₃CN/H₂O (0.1% CF₃COOH)) of the reaction mixture indicated complete conversion to a less polar product. The reaction mixture was diluted with aqueous acetic acid (40 ml H₂O, 40 ml CH₃COOH) and chromatographed. Reverse-phase (40 g, C18) flash column chromatography eluting with 20–60% CH₃CN/H₂O in 20% step gradients was followed by lyophilization of the appropriate fractions to provide 800 mg of the crude product. Preparative HPLC (RP-C 18, 50% CH₃CN/H₂O (0.1% CF₃COOH) gave 400 mg of the azide intermediate as the trifluoroacetate salt. Yield=39%.

¹H NMR (400 MHz, CD₃OD) δ 1.16 (d, J=6.1 Hz, 3H), 3.06 (t, J=7.2 Hz, 2H), 4.20 (dd, J=1.7 and 8.1 Hz, 1H), 4.97 (d, J=3.6 Hz, 1H), 5.15 (d, J=2.0 Hz, 1H), 6.74 (d, J=8.6 Hz, 2H), 7.11 (d, J=8.6 Hz, 2H). ESI-MS (M+H)⁺=1076.3.

Part D: CBZ Protection

To a stirred solution of the azide trifluoroacetate (Part C, 200 mg, 0.168 mmol) and triethylamine (0.035 ml, 0.252 mmol) in 2 ml of anhydrous N,N,-dimethylformamide was added benzyl 4-nitrophenyl carbonate (55.1 mg, 0.202 mmol). After a period of 3.5 h, HPLC analysis (RP-C18, 50% CH₃CN/H₂O (0.1% CF₃COOH)) of the reaction mixture indicated complete consumption of the starting material. The reaction mixture was then diluted with 2 ml water and chromatographed. Reverse-phase (8 g, C18) flash column chromatography eluting with 50–80% CH₃CN/H₂O in one 30% step gradient was followed by lyophilization of the appropriate fractions to provide 172 mg of the CBZ-protected azide (75% pure by analytical HPLC in 70% CH₃CN/H₂O (0.1% CF₃COOH)). Yield=65% (corrected for purity).

Part E: Azide Reduction

To a stirred solution of CBZ-protected azide (Part D, 122 mg, 0.102 mmol corrected for 75% purity) and triphenylphosphine (71.6 mg, 0.273 mmol) in tetrahydrofuran was added HPLC-grade water (5.5 ml, 0.305 mmol). After a period of 48 h, HPLC analysis (RP-C18, 70% CH₃CN/H₂O (0.1% CF₃COOH)) of the reaction mixture indicated greater than 90% conversion of starting material to a more polar product. The reaction mixture was concentrated prior to purification. Preparative HPLC (RP-C18, 50% CH₃CN/H₂O (0.1% CF₃COOH)) afforded 93 mg of mono-protected bisamine trifluoroacetate shown above. Yield=72%. ¹H NMR (500 MHz, CD₃OD) δ 1.16 (d, J=6.1 Hz, 3H), 3.26 (m, 1H), 3.33 (m, 1H), 4.06 (m, 1H), 4.18 (dd, J=1.6 and 8.0 Hz, 1H), 4.99 (d, J=3.2 Hz, 1H), 5.06 (ABq, J=12.5 Hz, 2H), 5.25 (d, J=2.1 Hz, 1H), 6.74 (d, J=8.5 Hz, 2H), 7.12 (d, J=8.5 Hz, 2H), 7.32 (m, 5H). ESI-MS (M+H)⁺=1184.6.

EXAMPLE 2

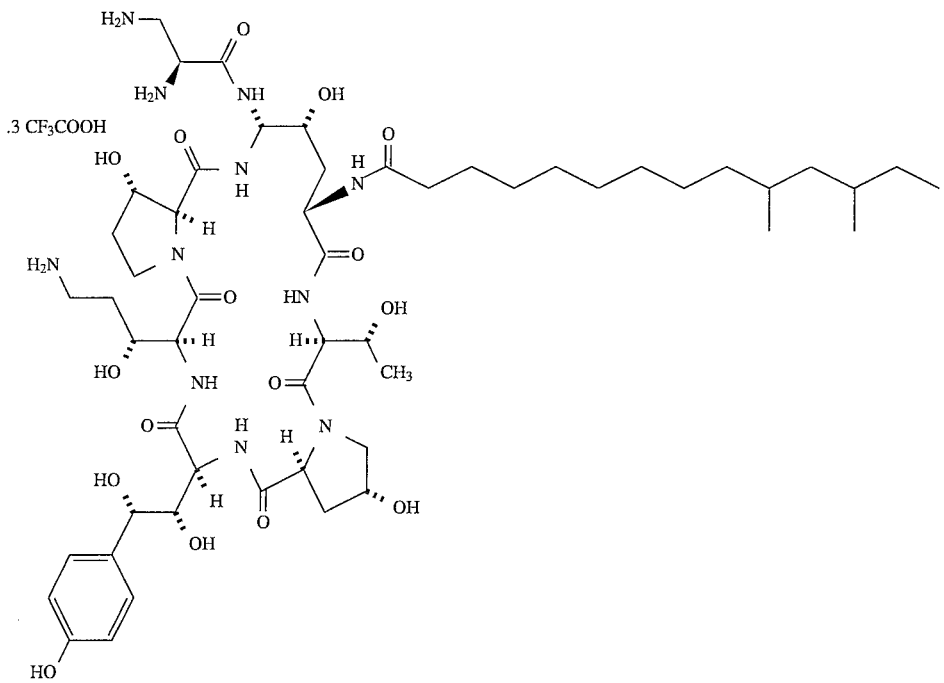

(SEQ ID NO. 3)

Part A

To a stirred suspension of L-α,β-diaminopropionic acid hydrochloride (1.0 g, 7.11 mmol) and N,N-diisopropylethylamine (4.96 ml, 28.45 mmol) in dichloromethane (freshly distilled from $CaH_2$) was added chlorotrimethylsilane (2.71 ml, 21.34 mmol). The reaction mixture was then refluxed for a period of 1.5 h and cooled to 0° C. Benzyl chloroformate (2.03 ml, 14.22 mmol) was added drop-wise at 0° C. and the mixture allowed to warm to 25° C. over a period of 1 h. The mixture was stirred at 25° C. for 18 h and then concentrated on a rotary evaporator prior to an extractive work-up. Partitioning was done with ethyl acetate/water (200 ml each). The organic layer was washed with 2×250 ml 1N HCl, 2×250 ml water, 1×250 ml brine, dried over magnesium sulfate and concentrated to give 2.4 g N,N-di-CBZ L-diaminopropionic acid.

$^1$H NMR (400 MHz, $CD_3OD$) δ 3.43 (dd, J-7.5 and 14.1 Hz, 1H), 3.60 (dd, J=4.6 and 14.1 Hz, 1H), 4.34 (dd, J=4.6 and 7.5 Hz, 1H), 5.06–5.08 (benzylic, 4H), 7.2–7.4 (m, 10H). ESI-MS $(M+H)^+=373.1$.

Part B

To a stirred solution of mono-protected bisamine trifluoroacetate (Ex. 1, Part E, 100.0 mg, 0.0785 mmol), N,N-diisopropylethylamine (15.1 gl, 0.0863 mmol), 1-(3-dimethyl-aminopropyl)-3-ethyl carbodiimide hydrochloride (33.0 mg, 0.1727 mmol), and 1-hydroxybenzotriazole hydrate (23.3 mg, 0.1727 mmol) in 2 ml of anhydrous N,N-dimethylformamide was added N,N-di-CBZ L-diaminopropionic acid (Part A, 64.6 mg, 0.1727 mmol). After a period of 5 h, HPLC analysis (RP-C18, 50% $CH_3CN/H_2O$ (0.1% $CF_3COOH$)) of the reaction mixture indicated complete conversion to a substantially less polar product. The reaction mixture was diluted with 1 mL water and chromatographed. Reverse-phase (4 g, C18) flash column chromatography eluting with 50–90% $CH_3CN/H_2O$ in one 40% step gradient was followed by lyophilization of the appropriate fractions to provide 103 mg of coupled product (75% pure by analytical HPLC, C18, 80% $CH_3CN/H_2O$ (0.1% $CF_3COOH$)).

Part C

To a stirred solution of the coupled product (Part B, 103 mg, 0.051 mmol corrected for 75% purity) in 5 ml methanol and 1 ml acetic acid was added 10% Pd/C (100mg). The mixture was stirred under an atmosphere of $H_2$ gas. After a period of 2 h, HPLC analysis (RP-C 18, $CH_3CN/H_2O$ (0.1% $CF_3COOH$)) indicated complete conversion to a more polar product. The catalyst was removed by filtration, rinsing with $CH_3OH$ and the filtrate was concentrated to dryness on a rotary evaporator prior to purification. Preparative HPLC (RP-C 18, 35% $CH_3CN/H_2O$ (0.1% $CF_3COOH$)) gave 54 mg of the amide (shown) as the tristrifluoroacetate salt. $^1$H NMR (500 MHz, $CD_3OD$) δ 1.18 (d, J=5.9 Hz, 3H), 3.08 (t, J=7.0 Hz, 2H), 3.24 (dd, J=7.6 and 13.6 Hz, 1H), 3.41 (dd, J=5.1 and 13.6 Hz, 1H), 4.21 (dd, J=1.6 and 8.0 Hz, 1H), 4.98 (dd, J=3.2 and 8.3 Hz, 1H), 5.64 (d, J=2.5 Hz, 1H), 6.74 (d, J=8.7 Hz, 2H), 7.11 (d, J=8.7 Hz, 2H). ESI-MS $(M+H)^+=1136.9$.

EXAMPLE 3

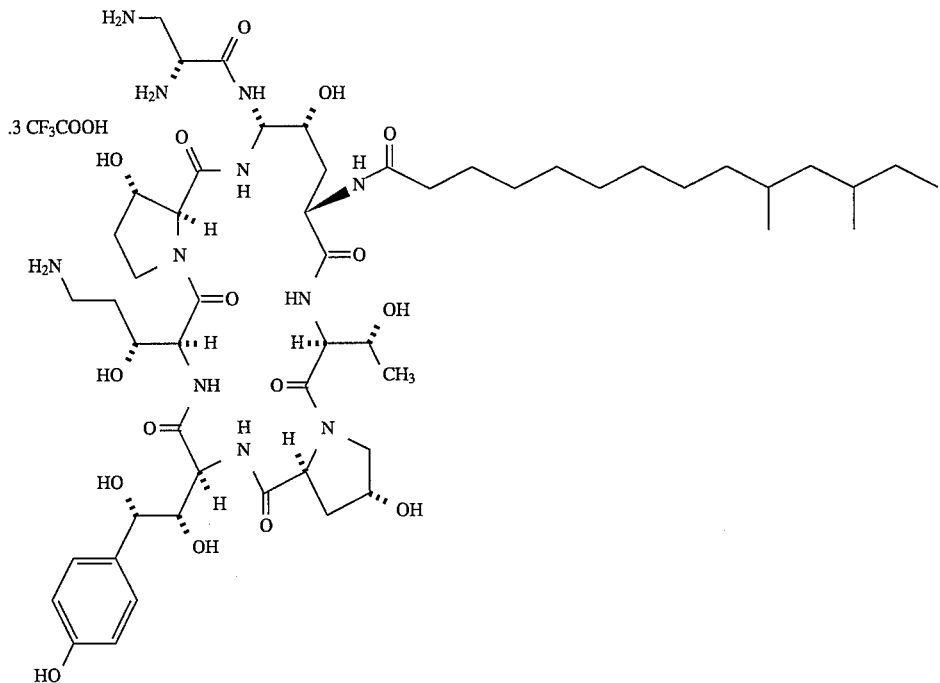

(SEQ ID NO. 3)

Part A

The N,N-di-CBZ D-diaminopropionic acid was prepared in a manner similar to that in Example 2, Part A.

$^1$H NMR (400 MHz, CD$_3$OD) δ 3.43 (dd, J=7.5 and 14.1 Hz, 1H), 3.60 (dd, J=4.6 and 14.1 Hz, 1H), 4.34 (dd, J=4.6 and 7.5 Hz, 1H), 5.06–5.08 (benzylic, 4H), 7.2–7.4 (m, 10H). ESI-MS (M+H)$^+$=373.1.

Part B

The coupling procedure was similar to that in Example 2, Part B.

Part C

The deprotection was similar to Example 2, Part C. The D-diaminopropionamide (final product) is shown in the drawing above. $^1$H NMR (500 MHz, CD$_3$OD) δ 1.18 (d, J=6.1 Hz, 3H), 3.07 (t, J=6.9 Hz, 2H), 3.28 (dd, J=6.4 and 13.9 Hz, 1H), 3.39 (dd, J=4.8 and 13.9 Hz, 1H), 4.20 (dd, J=1.6 and 8.0 Hz, 1H), 4.97 (dd, J=3.2 and 8.2 Hz, 1H), 5.54 (d, J=2.3 Hz, 1H), 6.75 (d, J=8.7 Hz, 2H), 7.11 (d, J=8.4 Hz, 2H). ESI-MS (M+H)$^+$=1136.7

EXAMPLE 4

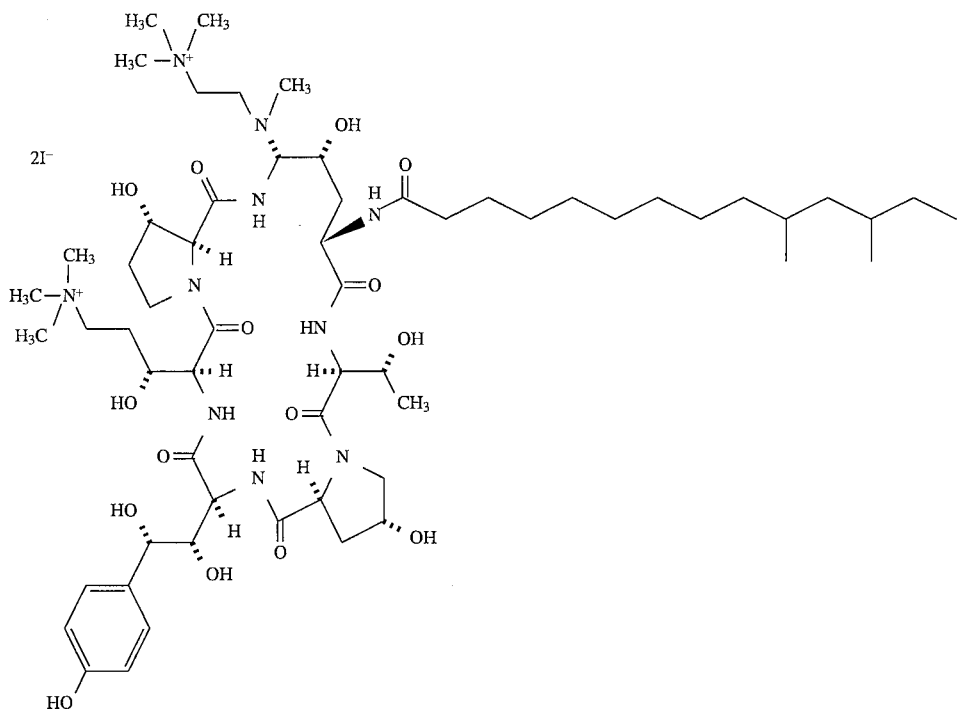

(SEQ ID NO. 3)

To a stirred solution of

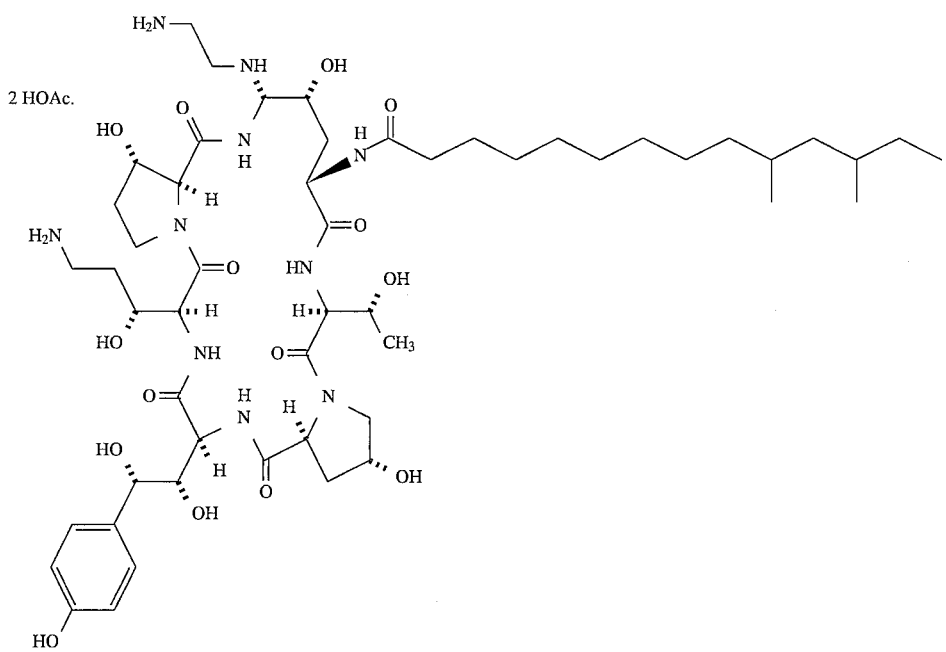

(100.0 mg, 0.079 mmol) and sodium bicarbonate (99.0 mg, 1.18 mmol) in 2.0 ml of anhydrous N,N-dimethylformamide was added methyl iodide (75.0 ml, 1.21 mmol). After a period of 18 h, HPLC analysis (RP-C18, 40% $CH_3CN/H_2O$ (0.1% $CF_3COOH$))of the reaction mixture indicated >90% conversion to a less polar product. The reaction mixture was diluted with 4 ml $H_2O$ and chromatographed. Reverses phase (4 g, C18) flash column chromatography eluting with 15–40% $CH_3CN/H_2O$ in one 25% step gradient was followed by lyophilization of the appropriate fractions to provide 34 mg of the crude product. Preparative HPLC (RP-C18, 35% $CH_3CN/H_2O$ (0.1% $CF_3COOH$) gave (SEQ ID NO. 3)

17 mg of the bistrimethylammonium iodide (shown above). $^1$H NMR (500 MHz, $CD_3OD$) δ 1.19 (d, J=6.2 Hz, 3H), 2.40 (s, 3H), 3.17 (s, 9H), 3.18 (s, 9H), 4.12 (m, 1H), 4.36 (dd, J=5.9 and 13.1 Hz, 1H), 4.91 (dd, J=6.7 and 9.2 Hz, 1H), 4.96 (dd, I=3.1 and 8.3 Hz, 1H), 6.75 (d, J=8.7 Hz, 2H), 7.12 (d, J=8.5 Hz, 2H) ESI-MS $(M+H)^{2+}$=596.7.

EXAMPLE 5

(SEQ ID NO. 3)

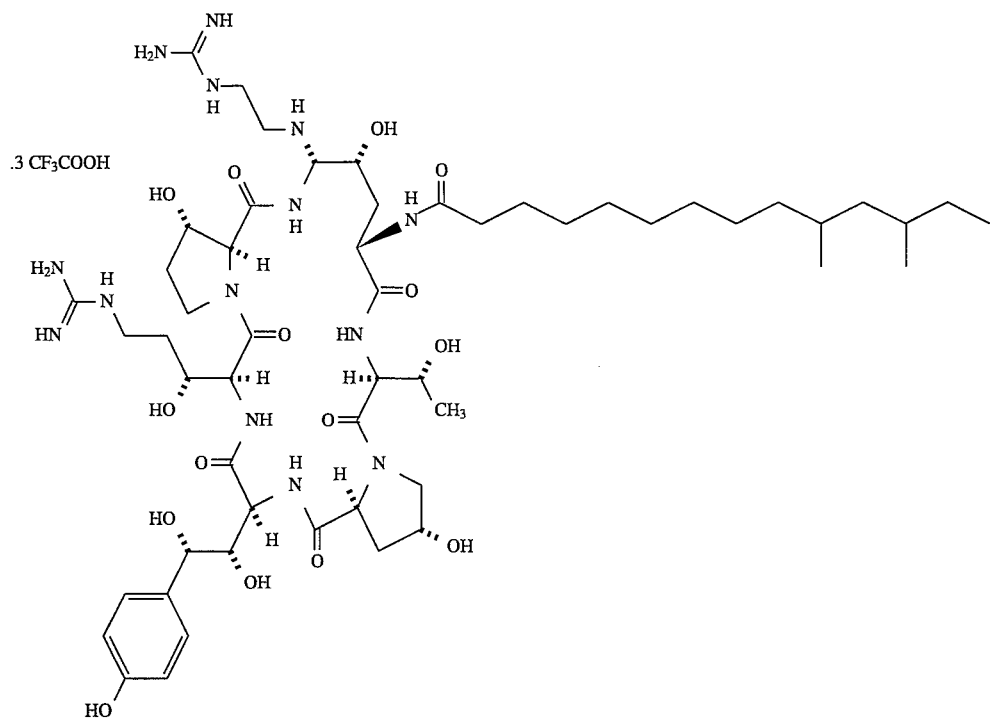

To a stirred solution of the starting compound of Example 4 (100.0 mg, 0.079 mmol) and formamidine sulfonic acid (prepared according to: *Tet Lett.,* 29 (26), p.3183, 1988) (58.4 mg, 0.471 mmol) in 2.5 ml of methanol was added 1M sodium bicarbonate (0.26 ml, 0.260 mmol). After a period of 18 h, HPLC analysis (RP-C18, 40% $CH_3CN/H_2O$ (0.1% $CF_3COOH$)) of the reaction mixture indicated complete conversion to a less polar product. The reaction mixture was diluted with 6 ml $H_2O$ and chromatographed. Reverse-phase (4 g, C18) flash column chromatography eluting with 15–40% $CH_3CN/H_2O$ in one step gradient was followed by lyophilization of the appropriate fractions to provide 80 mg of the crude product. Preparative HPLC (RP-C18, 35% $CH_3CN/H_2O$ (0.1% $CF_3COOH$) gave 38 mg of the bis-guanidine as the tristrifluoroacetate salt (shown in the drawing above). $^1$H NMR (500 MHz, $CH_3OD$) δ 1.17 (d, J=6.1 Hz, 3H), 2.43 (dd, J=6.9 and 12.9 Hz, 1H), 3.10 (m(br), 2H), 3.24 (m, 1H), 3.44 (m, 1H), 3.54 (m, H), 3.79 (dd, 7.3 and 17.6 Hz, 2H), 4.17 (dd, J=1.6 and 8.2 Hz, 1H), 4.23 (d, J=5.9 Hz, 1H), 4.54 (dd, J=6.9 and 11.7 Hz, 1H), 5.00 (dd, J=3.4 and 8.4 Hz, 1H), 5.14 (s(br), 1H), 6.75 (d, J=8.7 Hz, 2H), 7.11 (d, J=8.5 Hz, 2H). ESI-MS $(M+H)^+$=1177.7.

EXAMPLE 6

(SEQ ID NO. 3)

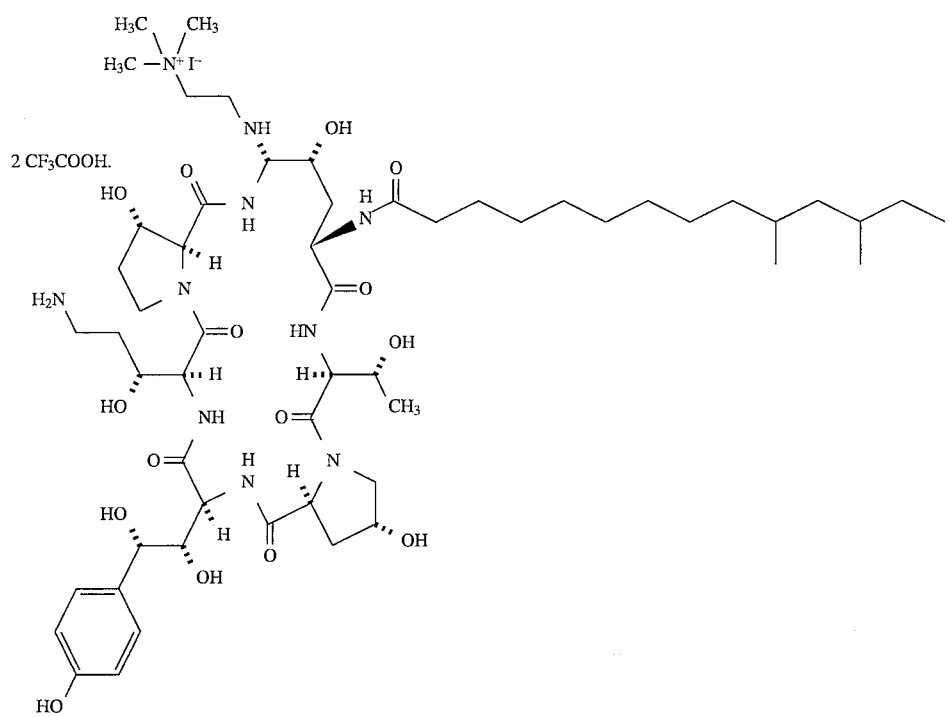

Part A

To a stirred solution of the nor-thioether (Example 1, Part A; 3.35 g, 2.50 mmol) in 55 ml of 1:1 acetonitrile/water was added OXONE® (1.6 g equivalent to 5.26 mmol of potassium peroxymonosulfate). After a period of 90 min, an additional 160 mg of OXONE® was added. After analysis by C 18-HPLC showed the conversion to a less polar product to be complete, the reaction mixture was lyophilized. Preparative C 18-HPLC of the lyophilizate eluting with 35% $CH_3CN/H_2O$ containing 0.1% $CF_3COOH$ was followed by lyophilization of the product-containing fractions to provide the sulfone intermediate. ESI-MS $(M+H)^+$ =1142.0

Part B

To a stirred solution of (2-aminoethyl)trimethylammonium chloride hydrochloride (1.3 g, 7.42 mmol) in water was added 5N NaOH (1.56 ml, 7.79 mmol). After 0.5 h, the solution was lyophilized to afford the amine.

Part C

To a stirred solution of the amine (Part B, 1.3 g, 7.42 mmol) in 5 mL of anhydrous N,N-dimethylformamide at 60° C. was added the nor-sulfone bistrifluoroacetate (Part A, 345 mg, 0.252 mmol). After a period of 1 h, HPLC analysis (RP-C18, 40% $CH_3CN/H_2O$ (0.1% $CF_3COOH$)) of the reaction mixture indicated complete conversion to a less polar product. The reaction mixture was diluted with aqueous acetic acid (12 ml $H_2O$, 6 ml $CH_3COOH$) and chromatographed. Reverses phase (C18) flash column chromatography eluting with 5–30% $CH_3CN/H_2O$ (0.1% $CF_3COOH$) in one step gradient was followed by lyophilization of the appropriate fractions to provide 80 mg of the crude product. Preparative HPLC (RP-C18, 35% $CH_3CN/H_2O$ (0.1% $CF_3COOH$)) gave 38 mg of the quaternary ammonium compound (shown above):

Yield=12%.

$^1$H NMR (500 MHz, $CH_3OD$) δ 1.17 (d, J=6.1 Hz, 3H), 1.84 (m, 1H), (2.44 (dd, J=6.6 and 12.8 Hz, 1H), 3.07 (t, J=6.8 Hz, 2H), 3.19 (s, 9H), 3.51 (t, J=6.8 Hz, 2H), 3.97 (dd, J=3.2 and 11.0 Hz, 1H), 4.18 (d, J=5.7 Hz, 1H), 4.21 (dd, J=1.5 and 8.0 Hz, 1H), 4.92 (dd, J=5.8 and 8.8 Hz, 1H), 4.99 (dd, J=3.2 and Hz, 1H), 6.75 Hz (d, J=8.6 Hz, 2H), 7.11 (d, J=8.6 Hz, 2H). ESI-MS $(M+H)^+$=1136.0.

EXAMPLE 7

(SEQ ID NO. 3)

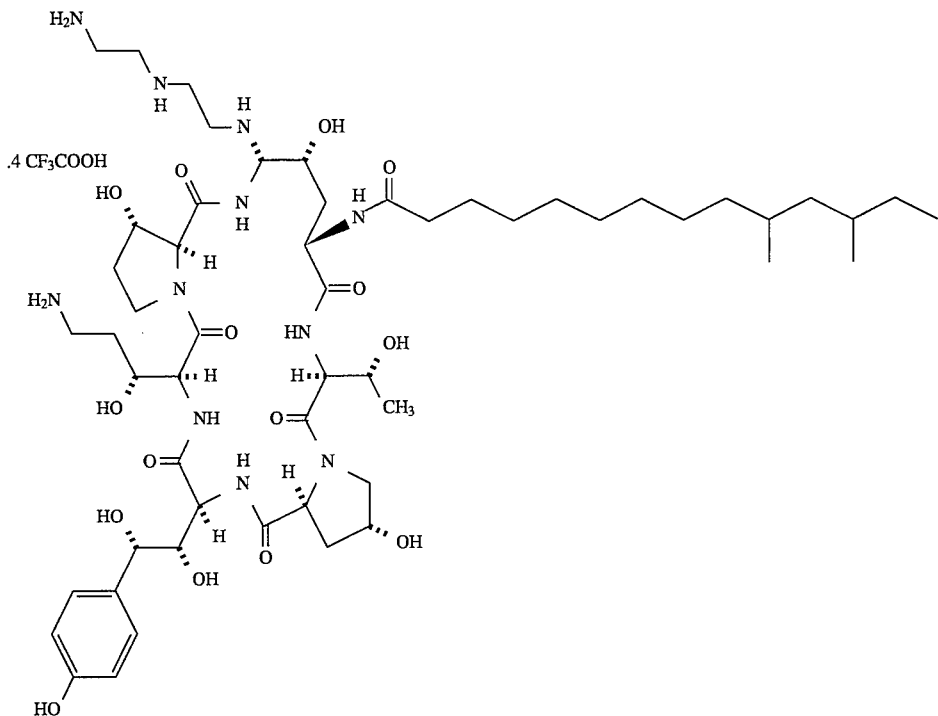

To neat diethylenetriamine (2 ml, 18.50 mmol) was added the nor-sulfone bistrifluoroacetate (Ex. 6 Part A, 276 mg, 0.20 mmol). After a period of 0.5 h, HPLC analysis (RP-C 18, 40% $CH_3CN/H_2O$ (0.1% $CF_3COOH$)) of the reaction mixture indicated complete conversion to more polar products. The reaction mixture was diluted with aqueous acetic acid (12 ml $H_2O$, 6 ml $CH_3COOH$) at 0° C. and chromatographed. Reverse-phase (C18) flash column chromatography eluting with 5–30% $CH_3CN/H_2O$ (0.1% $CF_3COOH$) in one 25% step gradient was followed by lyophilization of the appropriate fractions to provide 92 mg of the crude major product. Preparative HPLC (RP-C 18, 30% $CH_3CN/H_2O$ (0.1% $CF_3COOH$)) gave 47 mg of the above compound. $^1$H NMR (500 MHz, $CH_3OD$) δ 1.16 (d, J=6.1 Hz, 3H), 2.44 (dd, J=6.9 and 13.3 Hz, 1H), 3.04–3.24 (m, 10H), 3.77–3.87 (m, 3H), 3.98 (dd, J=3.0 and 11.1 Hz, 1H), 4.05 (m, 1H), 4.20 (dd, J=1.7 and 8.3 Hz, 1H), 4.48 (dd, J=2.5 and 5.0 Hz, 1H), 4.54 (dd, J=7.0 and 11.6 Hz, 1H), 4.99 (d, J=3.3 Hz, 1H), 5.05 (d, J=2.3 Hz, 1H), 6.75 Hz (d, J=8.7 Hz, 2H), 7.11 (d, J=8.5 Hz, 2H). ESI-MS $(M+H)^+$=1136.9.

EXAMPLE 8

(SEQ ID NO. 3)

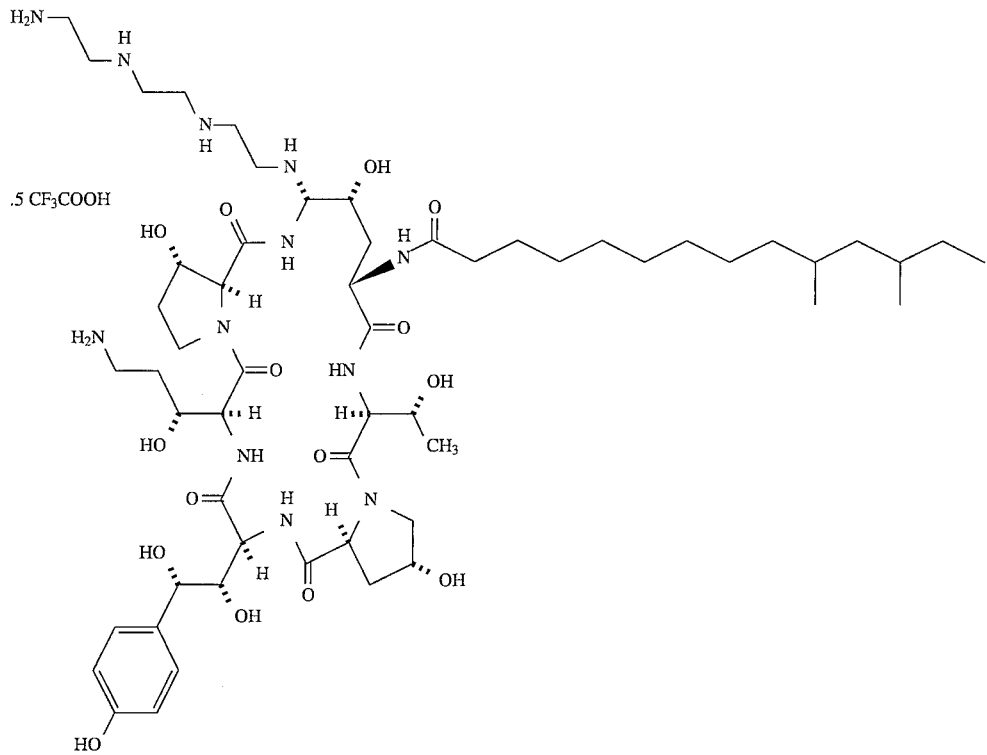

The displacement reaction was done in an analogous fashion to Example 7 with triethylenetetraamine used to displace the nor-sulfone. Preparative HPLC (RP-C18, 30% $CH_3CN/H_2O$ (0.1% $CF_3COOH$)) gave 55 mg of the above compound. $^1H$ NMR (500 MHz, $CH_3OD$) δ 1.16 (d, J=6.0 Hz, 3H), 2.44 (dd, J=6.9 and 13.3 Hz, 1H), 3.06 (m, 2H), 3.14–3.36 (m, 10H), 3.77–3.87 (m, 3H), 3.98 (dd, J=3.0 and 11.1 Hz, 1H), 4.05 (m, 1H), 4.20 (dd, J=1.7 and 8.3 Hz, 1H), 4.48 (dd, J=2.5 and 5.0 Hz, 1H), 4.54 (dd, J=7.0 and 11.6 Hz, H), 4.99 (dd, J=3.2 and 8.4 Hz, 1H), 5.15 (d, J=1.8 Hz, 1H), 6.75 Hz (d, J=8.5 Hz, 2H), 7.11 (d, J=8.7 Hz, 2H). ESI-MS $(M+H)^+=1179.7$.

EXAMPLE 9

(SEQ ID NO. 3)

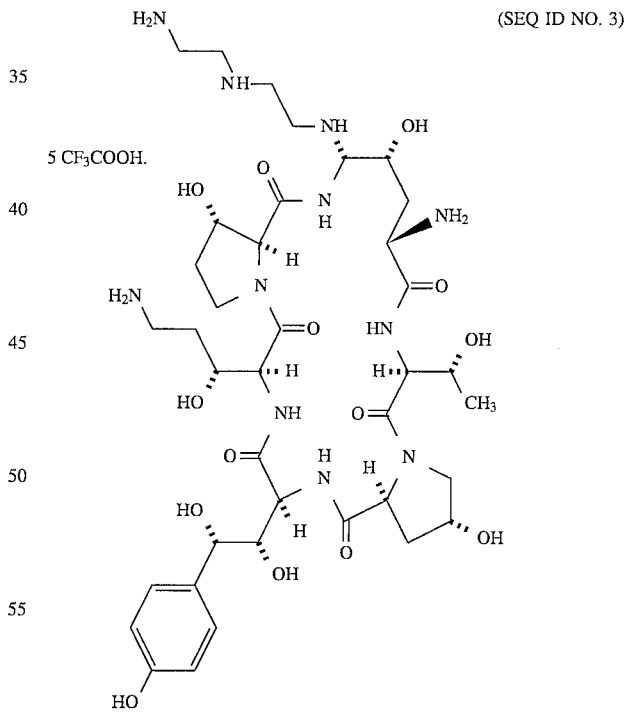

Part A: Preparation of the Deacylating Enzyme

*P. acidovorans* ATCC 53942, maintained on Luria-Bertani medium agar slants was used to produce the deacylation enzyme.

A seed culture was prepared by inoculating a 50-ml portion of Luria-Bertani medium in a 250 ml flask with a loopful of the bacterium and the culture was incubated for about 24 hours at 27° C. with constant shaking. Cells for the deacylation were grown by inoculating 15 liters of Luria-Bertani medium in a stirred fermentor with 30 ml of the seed culture and incubating with agitation of 400 rpm and aeration at 7.5 liters/min. at 28° C. for 20 to 24 hours. The cells were washed with 50 mM potassium phosphate buffer, pH 7.5 and resuspended in about 4 liters of the same buffer. The suspension was equilibrated to 37° C. to obtain the deacylating enzyme.

Part B: Deacylation

A compound of the structure

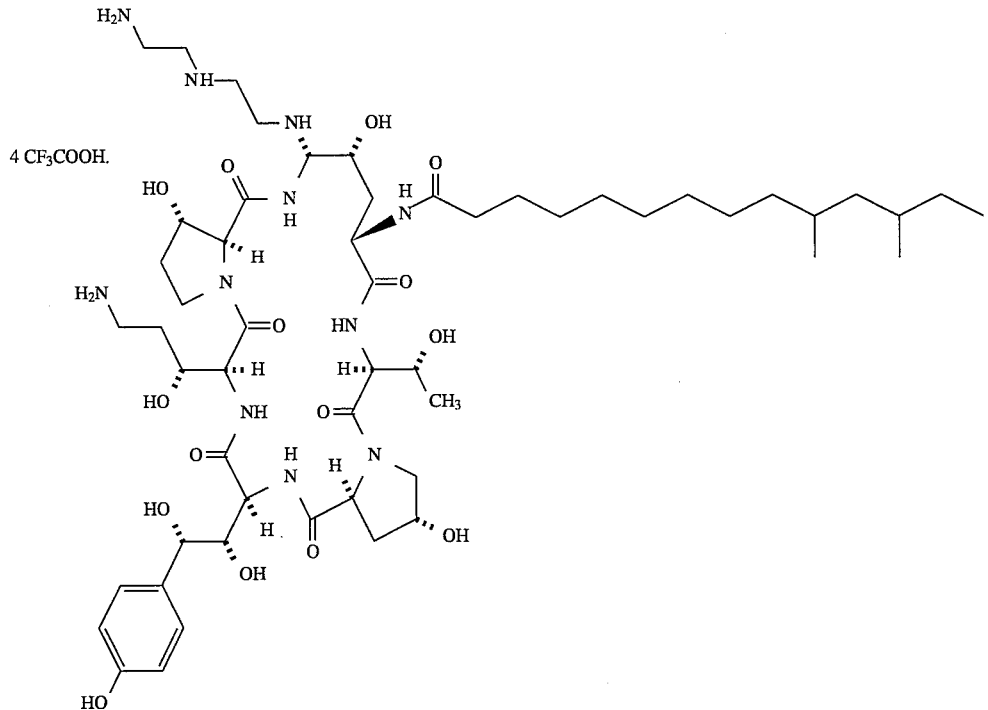

(3.5 g) is dissolved in 900 ml of distilled water and added slowly over a 1 hour period to 2 liters of the suspension of *P. acidovorans* cells from Part A. The resulting mixture is maintained at 37° C. while stirring at about 300 rpm without aeration. After 24 hours, the deacylation mixture is cleared of *P. acidovorans* cells by centrifugation and the nucleus is isolated from the supernatant by C18-high pressure liquid chromatography. Elution with 0–2% $CH_3CN/H_2O$ containing 0.1% $CF_3COOH$ in 0.5% step gradients is followed by lyophilization of the nucleus-containing fractions to give the deacylated product shown above as the pentakistrifluoroacetate salt: $C_{48}H_{68}F_{15}N_{11}O_{24}$, formula weight=1468.1.

EXAMPLE 10

(SEQ ID NO. 3)

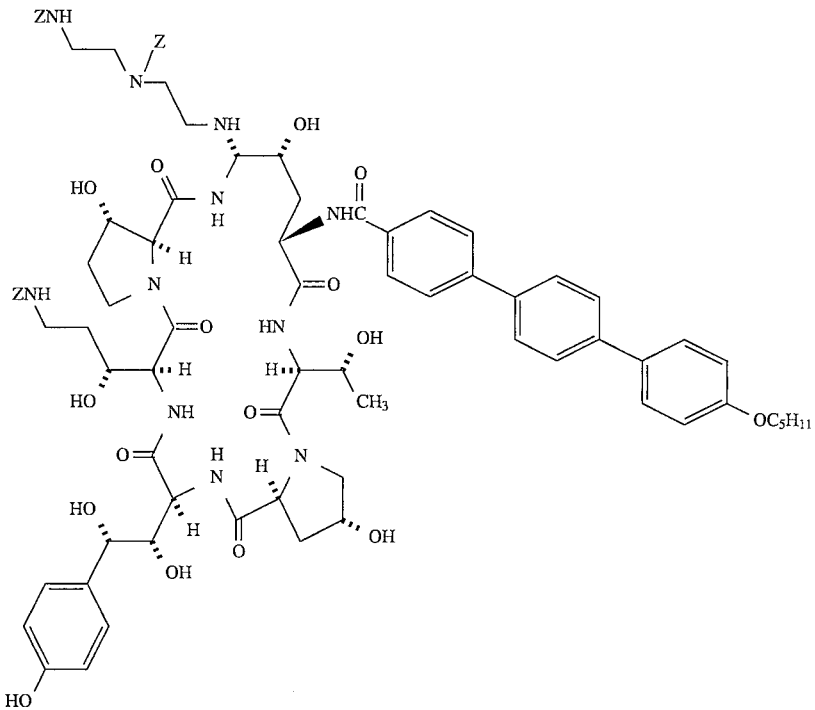

(SEQ ID NO. 3)

Part A: 4-(n-Pentoxyphenyl)-4'-pentafluorophenoxy-carbonylbiphenyl

Step 1: 4-(4-n-Pentoxyphenyl)bromobenzene

To a stirred solution of 4-(4-bromophenyl)phenol (25.5 g, 0.102 mol) in 400 mL of dimethylsulfoxide was added 2.5N NaOH (40.9 ml, 0.102 mol) followed by n-pentyl bromide (12.7 mL, 0.102 mol). The resulting mixture was heated at 70° C. for a period of 18 h. After cooling, the yellow solution was partitioned between ethyl acetate (1000 ml) and water (500 ml). The organic phase was washed with water (3×) and brine and dried with magnesium sulfate. The solvent was removed in vacuo to give 4-(4-n-pentoxyphenyl)bromobenzene (30.9 g): $^1$H NMR (400 MHz, DMSO-$d_6$) δ 0.93 (t, 3, J=7.2 Hz), 1.41 (m, 4), 1.79 (m, 2), 3.97 (t, 2, J=6.6 Hz), 6.94 (d, 2, J=8.8 Hz), 7.39 (d, 2, J=8.6 Hz), 7.45 (d, 2, J=8.8 Hz), 7.51 (d, 2, J=8.6 Hz).

Step 2; 4-(4-n-Pentoxyphenyl)phenylboronic acid

To a stirred suspension of 4-(4-n-pentoxyphenyl)bromobenzene (1.0 g, 3.13 mmol) in anhydrous tetrahydrofuran (20 ml) at −78° C. under a nitrogen atmosphere was added n-butyllithium in hexanes (2.5M, 1.32 ml, 3.30 mmol). After a period of 15 min, triisopropylborate (760 μl, 3.30 mmol) was added. Stirring at −78° C. was continued for 15 min and then at 25° C. for 40 min. The mixture was acidified with 0.5N HCl (20 mL) and then partitioned between ether (50 ml) and water (40 ml). The organic phase was washed with water (3×) and brine and dried with magnesium sulfate. The solvent was removed in vacuo to give 4-(4-n-pentoxyphenyl)phenylboronic acid (750 mg) as a white solid: $^1$H NMR (400 MHZ, DMSO-$d_6$) δ 0.89 (t, 3, J=7.2 Hz), 1.38 (m, 4), 1.72 (m, 2), 3.99 (t, 2, J=6.5 Hz), 6.99 (d, 2, J=8.8 Hz), 7.57 (d, 2, J=8.2 Hz), 7.60 (d, 2, J=8.8 Hz), 7.83 (d, 2, J=8.2 Hz).

Step 3: 4-(n-Pentoxyphenyl)-4'-carboxybiphenyl

To a stirred mixture of 4-(4-n-pentoxyphenyl)phenylboronic acid (1.0 g, 3.52 mmol) and 4-iodobenzoic acid (874 mg, 3.52 mmol) in ethanol (11 ml) and toluene (30 ml) was added an aqueous solution of sodium carbonate (2M, 5.3 ml, 10.6 mmol) followed by tetrakis-(triphenylphosphine)palladium (204 mg, 5 mol %). The reaction mixture was heated at 100° C. under a nitrogen atmosphere for a period of 18 h. The cooled mixture was acidified to pH 3 (1N HCl) and partitioned between ethyl acetate and water. The organic phase was washed with water (3×) and brine, dried with magnesium sulfate, and filtered through a bed of Celite. The solvent was removed in vacuo to give crude product which was purified by flash silica gel chromatography to provide 4-(n-pentoxyphenyl)-4'-carboxybiphenyl (450 mg): $^1$H NMR (400 MHz, DMSO-$d_6$) δ 0.89 (t, 3), 1.37 (m, 4), 1.72 (m, 2), 3.98 (t, 2), 7.01 (d, 2).

Step 4: 4-(n-pentoxyphenyl)-4'-pentafluorophenoxy-carbonylbiphenyl

To a mixture of 4-(n-pentoxyphenyl)-4'-carboxybiphenyl (3.04 g, 8.43 mmol) and dicyclohexylcarbodiimide (2.28 g, 11.1 mmol) in N,N-dimethylformamide (70 ml) at 0° C. was added pentafluorophenol (4.08 g, 22.2 mmol). The mixture was stirred at 25° C. for a period of 18 h. It was then partitioned between ethyl acetate and water. The organic phase was washed with water (3×) and brine and dried with magnesium sulfate. The solvent was removed in vacuo to give 3.95 g of pentafluorophenyl ester. Trituration of the crude ester with ether and hexane provided 0.5 g of clean 4-(n-pentoxyphenyl)-4'-pentafluorophenoxycarbonylbiphenyl after suction-drying of the filter cake: $^1$H NMR (400 MHz, CDCl$_{13}$) δ 0.93 (t, 3), 4.01 (t, 2), 6.98 (d, 2) 7.56 (d, 2), 7.67 (d, 2), 7.70 (d, 2), 7.79 (d, 2), 8.26 (d, 2).

Part B: Protection and Reacylation of the Nucleus

To a stirred solution of the nucleus (114 mg, 0.078 mmol) from Example 9 and benzyl 4-nitrophenylcarbonate (64 mg, 0.233 mmol) in anhydrous N,N-dimethylformamide (3.5 ml) is added triethylamine (54 gl, 0.390 mmol). The reaction mixture is stirred for a period of 1 hour. 4-(n-Pentoxyphenyl)-4'-pentafluorophenoxycarbonylbiphenyl (46 mg, 0.078 mmol) prepared as described in Part A is added and stirring is continued for a period of 60 hours. The reaction mixture is diluted with water (3.5 ml) and the product is isolated by C18 solid-phase extraction eluting initially with $CH_3CN/H_2O$ and then $CH_3OH$. Concentration of the product-containing $CH_3OH$ fractions as determined by analytical HPLC gives the product shown above: $C_{86}H_{103}N_{11}O_{22}$, molecular weight=1642.8.

(100 mg) for a period of 1.75 hours. The reaction mixture is filtered through a bed of diatomaceous earth to remove the catalyst, rinsing with MeOH. The filtrate is concentrated in vacuo. Preparative C18-HPLC of the residue, loaded in mobil phase containing sufficient $CH_3OH$ to fully solubilize, eluting with $CH_3CN/H_2O$ containing 0.1% $CF_3COOH$ is followed by lyophilization of the product-containing fractions as determined by analytical HPLC to give the product shown above as the tetrakistrifluoroacetate salt: $C_{70}H_{89}F_{12}N_{11}O_{24}$, formula weight=1696.5.

EXAMPLE 11

EXAMPLE 12

(SEQ ID NO. 3)

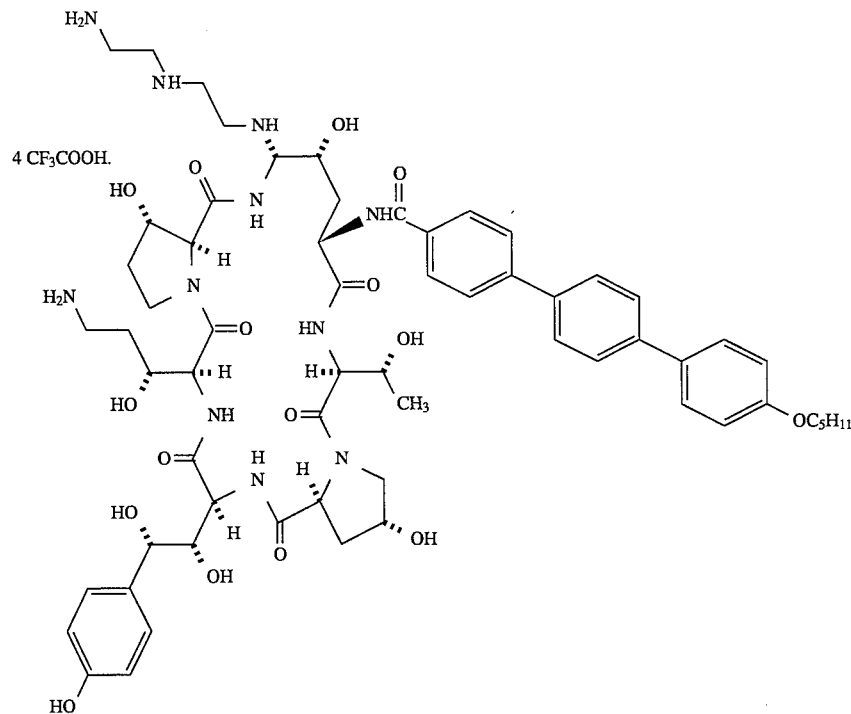

A solution of the tri-Z product from Example 10 in methanol (10 ml) and glacial acetic acid (4 ml) is hydrogenated under balloon pressure in the presence of 10% Pd/C

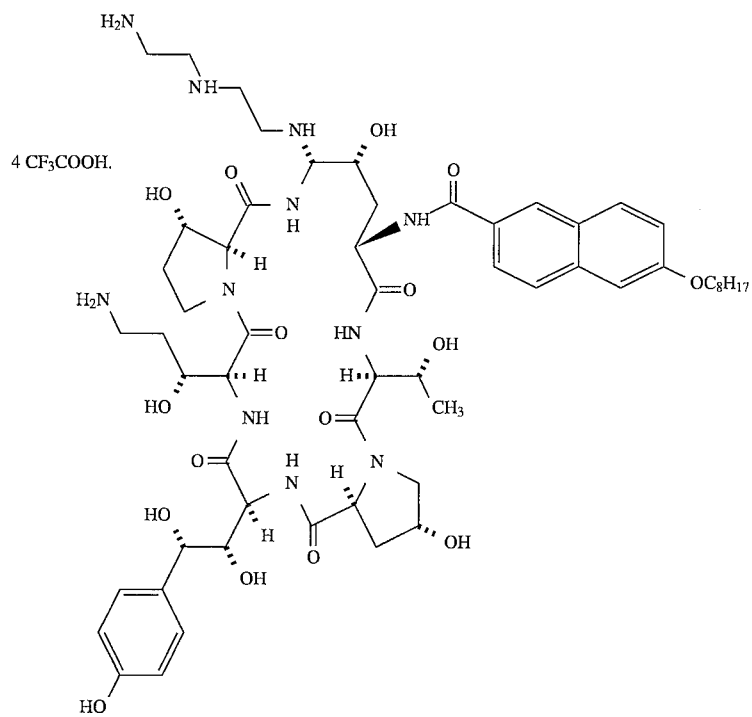

(SEQ ID NO. 3)

Part A: Preparation of Pentafluorophenyl 6-Octyloxy-2-naphthoate

To a suspension of 6-octyloxy-2-naphthoic acid (3.15 g, 10.5 mmol) and dicyclohexylcarbodiimide in ethyl acetate (25 ml) at 0° C. was added pentafluorophenol (2.12 g, 11.5 mmol). The mixture was stirred at 25° C. for a period of 18 h. The precipitate was removed by s filtration. The filtrate was washed with water (2×150 ml) and brine and dried with magnesium sulfate. Removal of the ethyl acetate in vacuo gave 5.4 g of pentafluorphenyl 6-octyloxy-2-naphthoate as a solid: $^1$H NMR (400 MHz, CH$_3$OD) δ 0.88 (t, 3, J=6.9 Hz), 4.10 (t, 2, J=6.6 Hz), 7.16 (d, 1), 7.21 (d, 1), 7.80 (d, 1), 7.87 (d,1), 8.08 (dd, 1), 8.69 (d, 1).

Part B: Protection and Reacylation of the Nucleus

The protected nucleus is prepared according to the procedure described in Example 10, Part B, and is reacylated with pentafluorophenyl 6-octyloxy-2-naphthoate: C$_{81}$H$_{10}$N$_{11}$O$_{22}$, molecular weight=1582.8.

Part C: Deprotection

The target compound as the tetrakistrifluoroacetate salt is prepared from the compound of Part B according to the procedure described in Example 11: C$_{65}$H$_{89}$F$_{12}$N$_{11}$O$_{24}$, formula weight=1636.5.

EXAMPLE 13

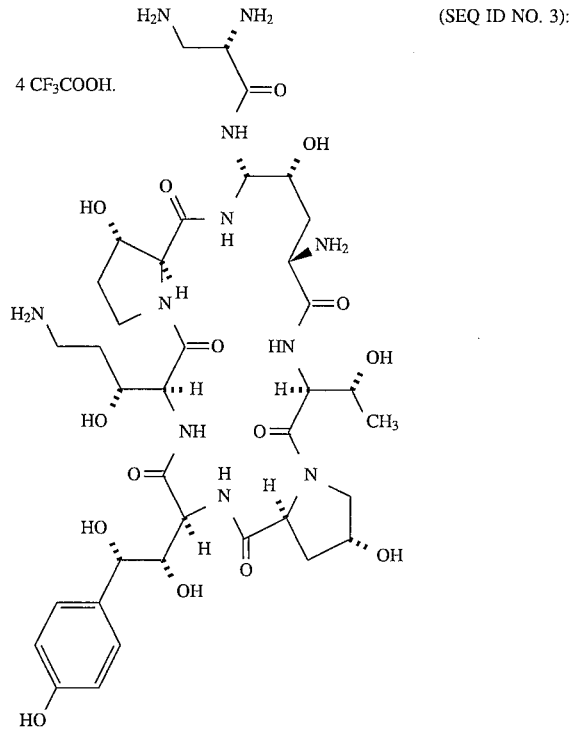

(SEQ ID NO. 3):

Part A: Preparation of the Deacylating Enzyme

*P. acidovorans* ATCC 53942, maintained on Luria-Bertani medium agar slants was used to produce the deacylation enzyme.

A seed culture was prepared by inoculating a 50-ml portion of Luria-Bertani medium in a 250 ml flask with a loopful of the bacterium and the culture was incubated for about 24 hours at 27° C. with constant shaking. Cells for the deacylation were grown by inoculating 15 liters of Luria-Bertani medium in a stirred fermentor with 30 ml of the seed culture and incubating with agitation of 400 rpm and aeration at 7.5 liters/min. at 28° C. for 20 to 24 hours. The cells were washed with 50 mM potassium phosphate buffer, pH 7.5 and resuspended in about 4 liters of the same buffer. The suspension was equilibrated to 37° C. to obtain the deacylating enzyme.

Part B: Deacylation

The compound prepared in Example 2 (3.5 g) is dissolved in 900 ml of distilled water and added slowly over a 1 hour period to 2 liters of the suspension of P. acidovorans cells from Part A maintained at 37° C. and stirred at about 300 rpm without aeration. After 24 hours, the deacylation mixture is cleared of P. acidovorans cells by centrifugation and the nucleus is isolated from the supernatant by C18-high pressure liquid chromatography. Elution with 0–2% $CH_3CN/H_2O$ containing 0.1% $CF_3COOH$ in 0.5% step gradients is followed by lyophilization of the nucleus-containing fractions to give the deacylated product as the tetrakistrifluoroacetate salt: $C_{45}H_{63}F_{12}N_{11}O_{23}$, formula weight=1354.0.

EXAMPLE 14

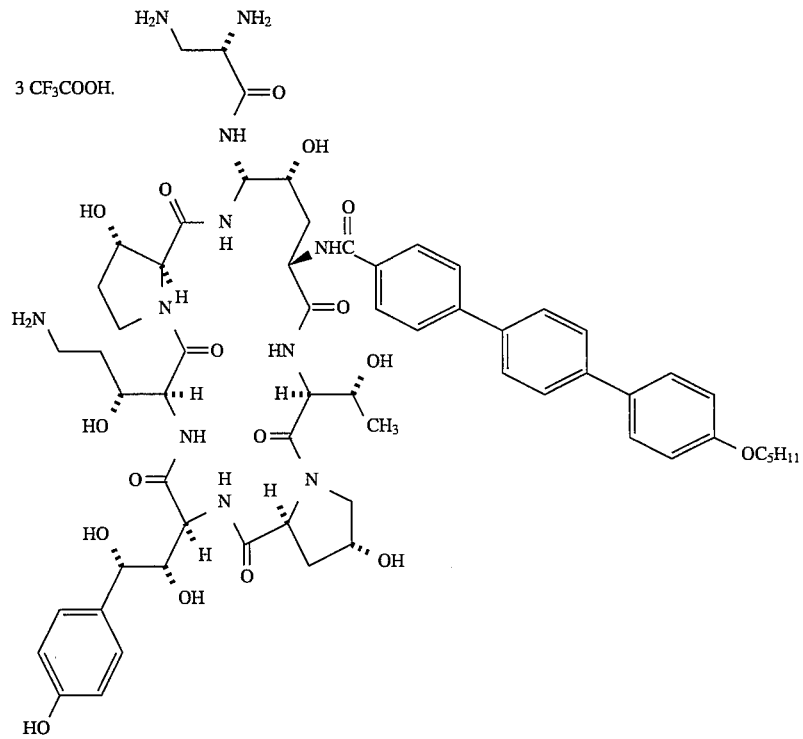

Part A: Protection and Reacylation

Following the procedure described in Example 10, Part B, the nucleus from Example 13 is selectively protected and reacylated with 4-(n-pentoxyphenyl)-4'-pentafluorophenoxycarbonylbiphenyl to give the tri-Z intermediate: $C_{85}H_{99}N_{11}O_{23}$, molecular weight=1642.8.

Part B: Deprotection

Following the procedure described in Example 11, the product from Part A is deprotected to give the product shown above as the tristrifluoroacetate salt: $C_{67}H_{84}F_9N_{11}O_{23}$, formula weight=1582.5.

COMPOSITION EXAMPLE A 1000 compressed tablets each containing 500 mg of the compound of Example 2 are prepared from the following formulation:

| Compound | Grams |
|---|---|
| Compound of Example 2 | 500 |
| Starch | 750 |
| Dibasic calcium phosphate, hydrous | 5000 |
| Calcium stearate | 2.5 |

The finely powdered ingredients are mixed well and granulated with 10 percent starch paste. The granulation is dried and compressed into tablets.

EXAMPLE B 1000 hard gelatin capsules, each containing 500 mg of the same compound are prepared from the following formulation:

(SEQ ID NO. 3)

| Compound | Grams |
|---|---|
| Compound of Example 2 | 500 |
| Starch | 250 |
| Lactose | 750 |
| Talc | 250 |
| Calcium stearate | 10 |

A uniform mixture of the ingredients is prepared by blending and used to fill two-piece hard gelatin capsules.

EXAMPLE C

An aerosol composition may be prepared having the following formulation:

|  | Per Canister |
| --- | --- |
| Compound of Example 2 | 24 mg |
| Lecithin NF Liquid Concd. | 1.2 mg |
| Trichlorofluoromethane, NF | 4.026 g |
| Dichlorodifluoromethane, NF | 12.15 g |

EXAMPLE D 250 milliliters of an injectible solution may be prepared by conventional procedures having the following formulation:

| Dextrose | 12.5 g |
| --- | --- |
| Water | 250 ml |
| Compound of Example 2 | 400 mg |

The ingredients are blended and thereafter sterilized for use.

PREPARATION OF STARTING MATERIALS

Compounds where $R'$ is dimethyltridecyl and $R_1$ is OH, $R_2$ is H, $R_3$ is $CH_2CONH_2$ and $R_4$ is $CH_3$ may be produced by cultivating Zalerion arboricola ATCC 20868 in nutrient medium with mannitol as the primary source of carbon as described in U.S. Pat. No. 5,021,341 issued Jun. 4, 1991.

Compounds in which $R_3$ is H and $R'$ is 11-methyltridecyl may be produced by cultivating Aspergillus sydowi in nutrient medium as described in J. Antibiotics XL (No. 3) p.28 (1987).

Compounds in which $R_3$ is $CH_3$ and $R'$ is linoleyl may be produced by cultivating Aspergillus nidulans NRRL 11440 in nutrient medium as described in U.S. Pat. No. 4,288,549 issued Sept. 8, 1981.

Compounds in which $R_3$ is $CH_2CN$ may be produced by the reaction of a compound having a carboxamide group in the corresponding position with excess cyanuric chloride in an aprotic solvent. Molecular sieves may be employed in this reaction. After completion of the reaction, the sieves, if employed, are removed, and the filtrate concentrated to obtain the nitrile compound as more fully described in U.S. Pat. No. 5,348,940 issued Sept. 20, 1994.

Compounds in which $R_3$ is $CH_2CH_2NH_2$ may be produced by either a chemical or catalytic reduction of the nitrile. It is conveniently carded out employing large molar excess of sodium borohydride with cobaltous chloride as more fully described in copending application Ser. No. 936,558 filed Sept. 3, 1992.

Compounds in which $R_5$ is OH or $OSO_3H$ are described in European Patent Applications 0 431 350 and 0 462 531 by Fujisawa Pharmaceutical Co., Ltd.

Starting materials in which $R'$ is a different group from that of the natural product may be obtained by deacylating the lipophilic group of the natural product by subjecting the natural product in a nutrient medium to a deacylating enzyme until substantial deacylation occurs, said enzyme having first been obtained by cultivating a microorganism of the family Pseudomondaceae or Actinoplanaceae, as described in Experentia 34, 1670 (1978) or U.S. Pat. No. 4,293,482, recovering the deacylated cyclopeptide, and thereafter acylating the deacylated cyclopeptide by mixing together with an appropriate active ester $R'COX$ to obtain Compound A with the desired acyl group.

The active esters $R'COX$ may be prepared by methods known to the skilled chemist as illustrated in the following examples. Although any active ester is appropriate, the compounds are illustrated with pentafluorophenyl esters.

Preparation of Alkoxy Biphenyl Side Chains

The biphenylcarboxylic acid esters may be obtained through the following sequence of reactions illustrated as follows:

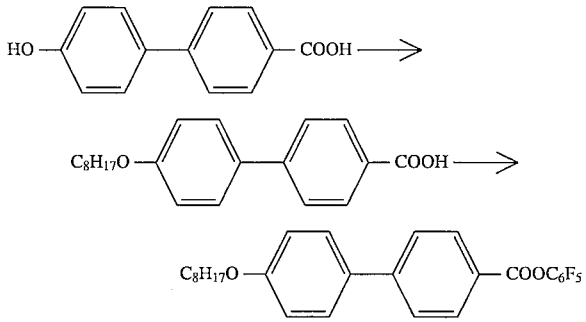

n-Octyl bromide (0.102 mol) is added to a solution of 4-(4-hydroxyphenyl)benzoic acid (0.102 mol) and 2.5N sodium hydroxide (0.102 mol) and the mixture stirred at 70° C. for a period of 18 hours. The reaction mixture is allowed to cool and then acidified to pH 3 and partitioned between ethyl acetate and water. The organic phase is washed with water and brine and the solvent then removed to obtain the 4'-noctyloxy[ 1,1'-biphenyl]-4-ylcarboxylic acid, $C_{21}H_{23}O_3$, M.W. 326.4

B. Preparation of pentafluorophenyl Ester

Pentafluorophenol (11.5 mmol) is added at 0° to a mixture of 10.5 mmol 4'-n-octyloxy[1,1'-biphenyl]-4-ylcarboxylic acid and 10.5 mmol of dicyclohexylcarbodiimide in ethyl acetate. The mixture is stirred at 25° C. for a period of 18 hours whereupon a precipitate is formed. The reaction mixture is filtered, the filtrate washed with water and brine and dried, the solvent removed in vacuo to obtain pentafluorophenyl 4'-n-octyloxy[1,1'-biphenyl]-4-ylcarboxylate, $C_{27}H_{25}F_5O_3$, M.W. 492.5.

Preparation of Aminoethyloxybiphenyl Side chains

Preparation of
4'-(2-[4-Cyclohexylmethylpiperidin-1-yl]ethoxy)
-[1,1'-biphenyl]-4-ylcarboxylic acid,
Pentafluorophenyl Ester

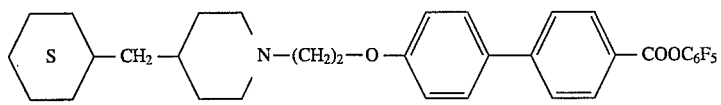

Part A: Preparation of 4-Cyclohexylmethylpiperidine

4-Benzylpiperidine is dissolved in glacial acetic acid containing $PtO_2$ (approximately 50 wt percent). A Paar hydrogenator is used and the reaction vessel is flushed with $H_2$ and pressurized to 3 atm. The mixture is shaken for sufficient time to give reduction of the aromatic ring to the fully saturated product which is determined by the uptake of 3 molar equivalents of $H_2$. The black solid is filtered and the acetic acid removed by evaporation under reduced pressure to obtain the product as an acetate salt.

Part B: Preparation of 1-(2-Hydroxyethyl)-4-cyclohexylmethyl-piperidine

The product from Part A (1.0 eq) is dissolved in dichloromethane containing an equimolar amount of diisopropylethyl amine. Ethylene oxide (10 eq) is added and the mixture is stirred until starting material is consumed. The desired product is obtained by removal of the solvent in vacuo followed by purification by column chromatography.

Part C: Preparation of 4'-(2-[4-cyclohexylmethylpiperidine-1-yl]ethoxy)-[1,1'-biphenyl]-4-ylcarboxylic acid 4'-Hydroxy-[1,1'-biphenyl-4-ylcarboxylic acid methyl ester (1.0 eq) is dissolved in dichloromethane and triphenylphosphine (1.3 eq) and the hydroxyethyl compound (1.0 eq) from Part B is added. Next, diethyl azodicarboxylate (1.3 eq) is added and the mixture is stirred until starting material is consumed. The mixture is diluted with dichloromethane and washed with water. The organic layer is dried with $MgSO_4$ and filtered. The solvent is removed in vacuo and the residue is dissolved in ethanol. An excess of 3N sodium hydroxide is added and the mixture stirred for several hours. The reaction is neutralized with 2N HCl and is extracted with ethyl acetate. The ethyl acetate layer is dried with $MgSO_4$, filtered and the solvent vaporized under reduced pressure. The desired product is obtained in substantially pure form by column chromatography.

Part D: Preparation of the Pentafluorophenyl Ester

The carboxylic acid (1.0 eq) and dicyclohexylcarbodiimide (1.0 eq) are dissolved in ethyl acetate and the solution is cooled to 0° C. Pentafluorophenol (1.05 eq) is added, the ice bath then is removed and the reaction stirred at ambient temperature for 18–24 h. An equal volume of ether is added, the mixture is filtered and the solvent removed in vacuo. The product (MW=587.64) may be obtained in a sufficiently pure form to be utilized for nucleus acylation.

Preparation of 4'-(2-[4-Undecylpiperizin-1-yl]-ethoxy)[1,1'-biphenyl]-4-ylcarboxylic acid, pentafluorophenyl Ester

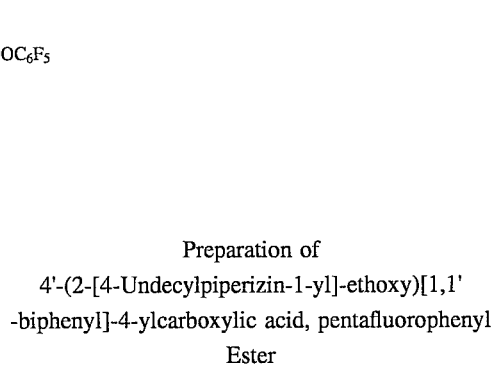

Part A: Preparation of 4-Undecylpiperazine

Excess piperazine (5 eq) and 1-bromoundecane (1.0 eq) are dissolved in dichloromethane and allowed to react overnight. The mixture is extracted with aqueous sodium bicarbonate and the organic layer dried with sodium sulfate. The mixture is filtered, the solvent removed in vacuo and the residue purified by column chromatography.

Part B: Preparation of 1-(2-Hydroxyethyl)-4-undecylpiperazine

The substituted piperazine above (1.0 eq) is dissolved in n-propanol and bromoethanol (1.0 eq) is added along with diisopropyl-ethyl amine (1.1 eq). After several hours, the solvent is removed in vacuo and the residue dissolved in dichloromethane. The organic layer is washed with water and then aqueous sodium bicarbonate. The organic layer is dried with $MgSO_4$ and filtered. Removal of the solvent in vacuo is followed by purification by column chromatography.

Part C: Preparation of the Carboxylic Acid

The procedure is essentially the same as describe in Part C above except that the hydroxyethyl piperazine from above is substituted for the hydroxyethyl piperidine.

Part D: Preparation of the Pentafluorophenyl Ester

The procedure is identical to Part D from above except that piperazinyl-substituted-biphenyl carboxylic acid is used. The product (MW=646.75) may be obtained in a sufficiently pure form to be utilized "as is" in nucleus acylation.

What is claimed is:
1. A compound selected from the group consisting of
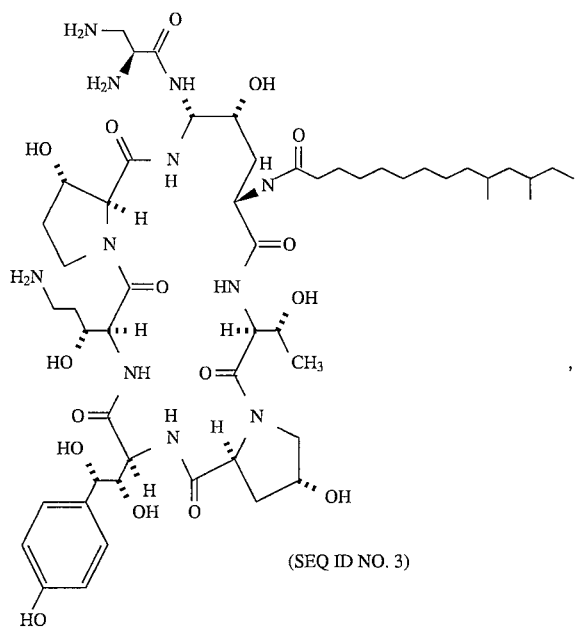
(SEQ ID NO. 3)
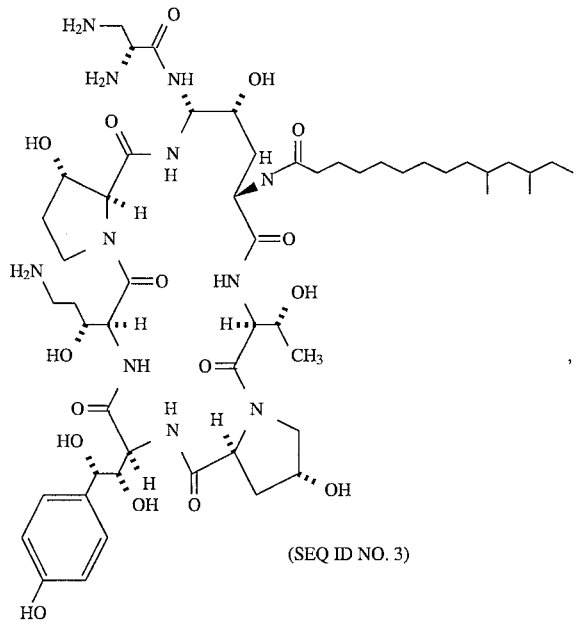
(SEQ ID NO. 3)
-continued
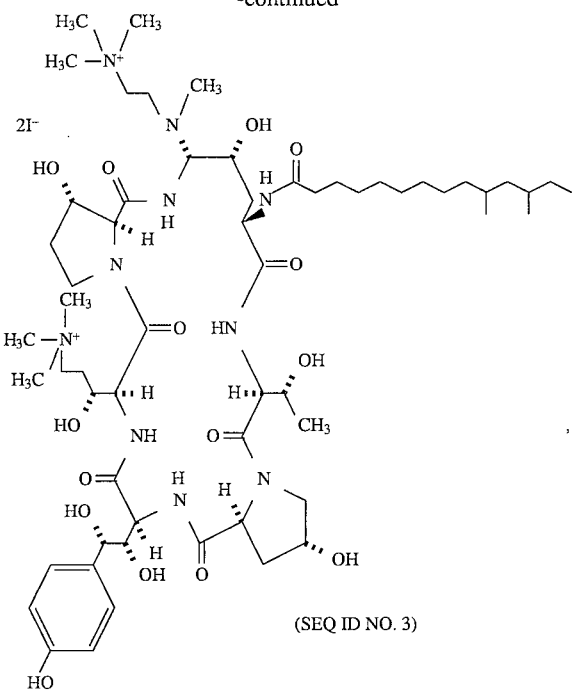
(SEQ ID NO. 3)
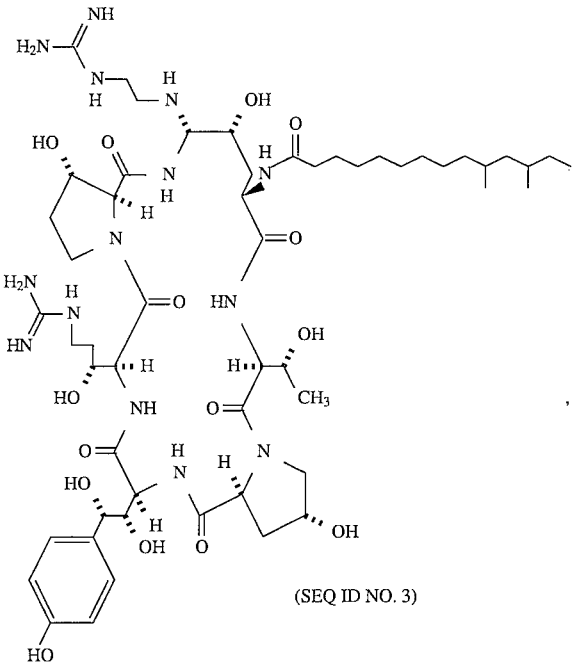
(SEQ ID NO. 3)

61
-continued
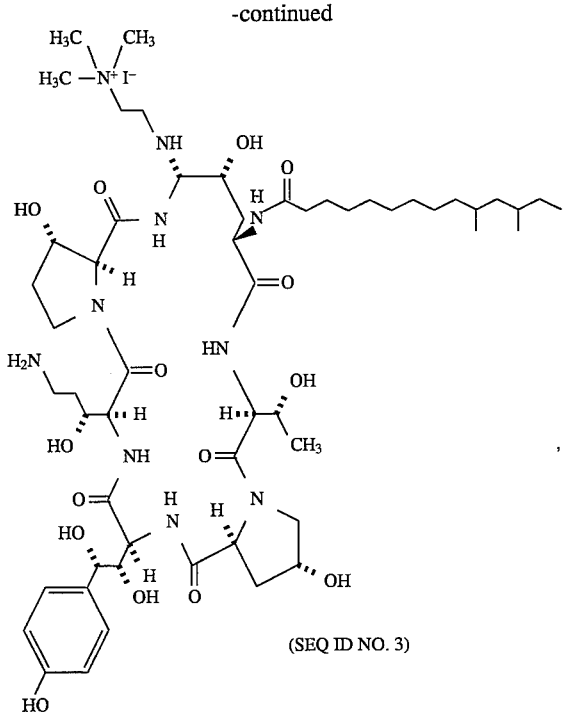
(SEQ ID NO. 3)
(SEQ ID NO. 3)
62
-continued
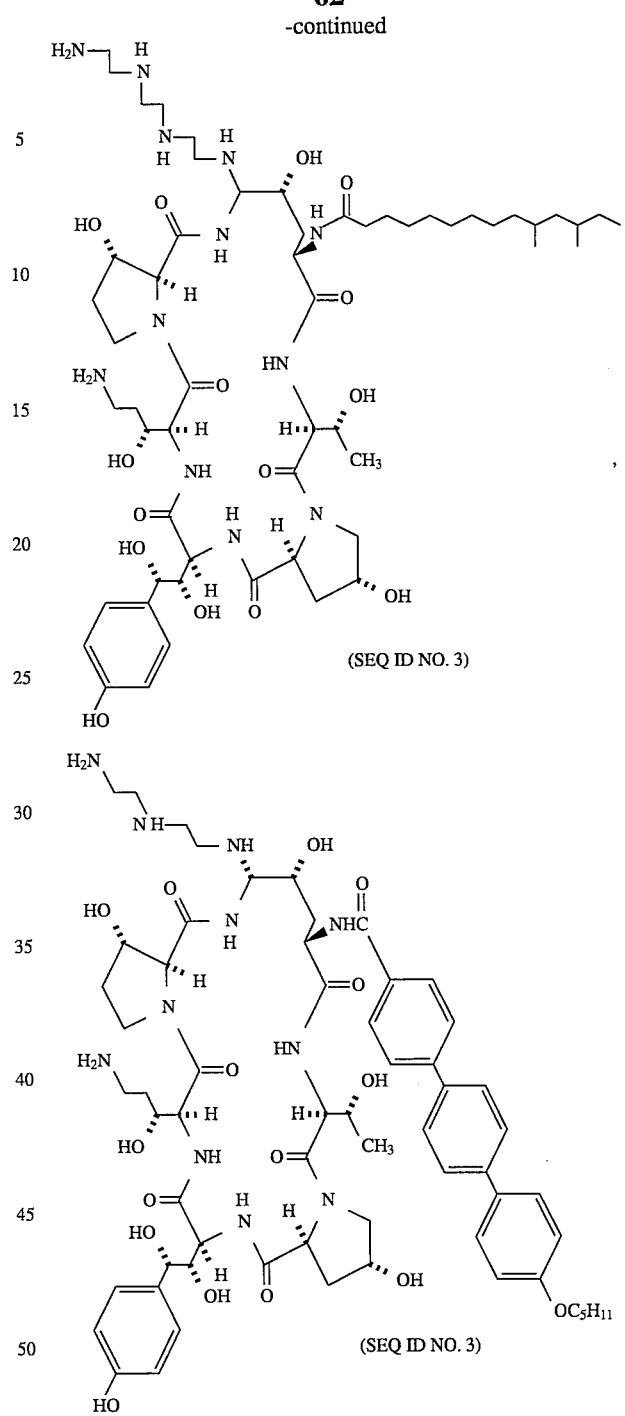
(SEQ ID NO. 3)
(SEQ ID NO. 3)

-continued

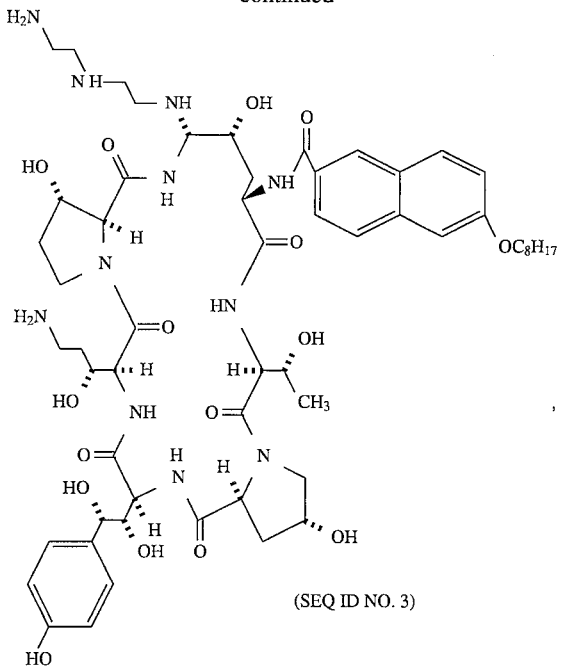

(SEQ ID NO. 3)

and

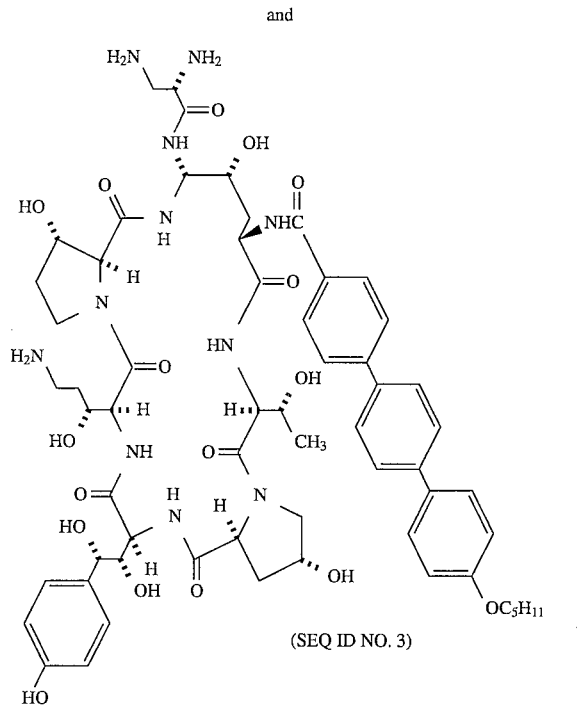

(SEQ ID NO. 3)

or a pharmaceutically acceptable salt thereof.

2. An antibiotic composition comprising an antimicrobial amount of a compound as defined in claim 1 in a pharmaceutically acceptable carrier.

3. A composition according to claim 2 in unit dosage form wherein the compound is present in an amount of 10 mg to 200 milligrams.

4. A method for treating mycotic infections comprising administering a therapeutic amount of a compound of claim 1 to a subject in need of therapy.

5. A method for treating *Pneumocystis carinii* infections which comprises administering a therapeutic amount of a compound as defined in claim 1.

\* \* \* \* \*

SEQUENCE LISTING ( 1 ) GENERAL INFORMATION:

( i i i ) NUMBER OF SEQUENCES: 24

( 2 ) INFORMATION FOR SEQ ID NO:1:

( i ) SEQUENCE CHARACTERISTICS:
( A ) LENGTH: 6 amino acids
( B ) TYPE: amino acid
( C ) STRANDEDNESS: unknown
( D ) TOPOLOGY: circular ( i i ) MOLECULE TYPE: peptide ( i i i ) HYPOTHETICAL: NO ( i v ) ANTI-SENSE: NO ( x i ) SEQUENCE DESCRIPTION: SEQ ID NO:1:

Xaa  Thr  Xaa  Xaa  Ser  Xaa
1                   5

( 2 ) INFORMATION FOR SEQ ID NO:2:

( i ) SEQUENCE CHARACTERISTICS:
( A ) LENGTH: 6 amino acids
( B ) TYPE: amino acid
( C ) STRANDEDNESS: unknown
( D ) TOPOLOGY: circular ( i i ) MOLECULE TYPE: peptide ( i i i ) HYPOTHETICAL: NO ( i v ) ANTI-SENSE: NO ( x i ) SEQUENCE DESCRIPTION: SEQ ID NO:2:

Xaa  Thr  Xaa  Xaa  Thr  Xaa
1                   5

( 2 ) INFORMATION FOR SEQ ID NO:3:

( i ) SEQUENCE CHARACTERISTICS:
( A ) LENGTH: 6 amino acids
( B ) TYPE: amino acid
( C ) STRANDEDNESS: unknown
( D ) TOPOLOGY: circular ( i i ) MOLECULE TYPE: peptide ( i i i ) HYPOTHETICAL: NO ( i v ) ANTI-SENSE: NO ( x i ) SEQUENCE DESCRIPTION: SEQ ID NO:3:

Xaa  Thr  Xaa  Xaa  Xaa  Xaa
1                   5

( 2 ) INFORMATION FOR SEQ ID NO:4:

( i ) SEQUENCE CHARACTERISTICS:
( A ) LENGTH: 6 amino acids
( B ) TYPE: amino acid
( C ) STRANDEDNESS: unknown
( D ) TOPOLOGY: circular ( i i ) MOLECULE TYPE: peptide ( i i i ) HYPOTHETICAL: NO ( i v ) ANTI-SENSE: NO ( x i ) SEQUENCE DESCRIPTION: SEQ ID NO:4:

Xaa Ser Xaa Xaa Ser Xaa
1               5

( 2 ) INFORMATION FOR SEQ ID NO:5:

( i ) SEQUENCE CHARACTERISTICS:
( A ) LENGTH: 6 amino acids
( B ) TYPE: amino acid
( C ) STRANDEDNESS: unknown
( D ) TOPOLOGY: circular ( i i ) MOLECULE TYPE: peptide ( i i i ) HYPOTHETICAL: NO ( i v ) ANTI-SENSE: NO ( x i ) SEQUENCE DESCRIPTION: SEQ ID NO:5:

Xaa Ser Xaa Xaa Thr Xaa
1               5

( 2 ) INFORMATION FOR SEQ ID NO:6:

( i ) SEQUENCE CHARACTERISTICS:
( A ) LENGTH: 6 amino acids
( B ) TYPE: amino acid
( C ) STRANDEDNESS: unknown
( D ) TOPOLOGY: circular ( i i ) MOLECULE TYPE: peptide ( i i i ) HYPOTHETICAL: NO ( i v ) ANTI-SENSE: NO ( x i ) SEQUENCE DESCRIPTION: SEQ ID NO:6:

Xaa Ser Xaa Xaa Xaa Xaa
1               5

( 2 ) INFORMATION FOR SEQ ID NO:7:

( i ) SEQUENCE CHARACTERISTICS:
( A ) LENGTH: 6 amino acids
( B ) TYPE: amino acid
( C ) STRANDEDNESS: unknown
( D ) TOPOLOGY: circular ( i i ) MOLECULE TYPE: peptide ( i i i ) HYPOTHETICAL: NO ( i v ) ANTI-SENSE: NO ( x i ) SEQUENCE DESCRIPTION: SEQ ID NO:7:

Xaa Thr Xaa Xaa Ser Xaa
1               5

( 2 ) INFORMATION FOR SEQ ID NO:8:

( i ) SEQUENCE CHARACTERISTICS:
( A ) LENGTH: 6 amino acids
( B ) TYPE: amino acid
( C ) STRANDEDNESS: unknown
( D ) TOPOLOGY: circular ( i i ) MOLECULE TYPE: peptide ( i i i ) HYPOTHETICAL: NO ( i v ) ANTI-SENSE: NO ( x i ) SEQUENCE DESCRIPTION: SEQ ID NO:8:

Xaa Thr Xaa Xaa Thr Xaa
1               5

( 2 ) INFORMATION FOR SEQ ID NO:9:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: circular ( i i ) MOLECULE TYPE: peptide ( i i i ) HYPOTHETICAL: NO ( i v ) ANTI-SENSE: NO ( x i ) SEQUENCE DESCRIPTION: SEQ ID NO:9:

Xaa Thr Xaa Xaa Xaa Xaa
1               5

( 2 ) INFORMATION FOR SEQ ID NO:10:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: circular ( i i ) MOLECULE TYPE: peptide ( i i i ) HYPOTHETICAL: NO ( i v ) ANTI-SENSE: NO ( x i ) SEQUENCE DESCRIPTION: SEQ ID NO:10:

Xaa Ser Xaa Xaa Ser Xaa
1               5

( 2 ) INFORMATION FOR SEQ ID NO:11:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: circular ( i i ) MOLECULE TYPE: peptide ( i i i ) HYPOTHETICAL: NO ( i v ) ANTI-SENSE: NO ( x i ) SEQUENCE DESCRIPTION: SEQ ID NO:11:

Xaa Ser Xaa Xaa Thr Xaa
1               5

( 2 ) INFORMATION FOR SEQ ID NO:12:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: circular ( i i ) MOLECULE TYPE: peptide ( i i i ) HYPOTHETICAL: NO ( i v ) ANTI-SENSE: NO ( x i ) SEQUENCE DESCRIPTION: SEQ ID NO:12:

Xaa Ser Xaa Xaa Xaa Xaa
1               5

( 2 ) INFORMATION FOR SEQ ID NO:13:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: circular ( i i ) MOLECULE TYPE: peptide ( i i i ) HYPOTHETICAL: NO ( i v ) ANTI-SENSE: NO ( x i ) SEQUENCE DESCRIPTION: SEQ ID NO:13:

Xaa Thr Xaa Xaa Ser Xaa
1               5

( 2 ) INFORMATION FOR SEQ ID NO:14:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: circular ( i i ) MOLECULE TYPE: peptide ( i i i ) HYPOTHETICAL: NO ( i v ) ANTI-SENSE: NO ( x i ) SEQUENCE DESCRIPTION: SEQ ID NO:14:

Xaa Thr Xaa Xaa Thr Xaa
1               5

( 2 ) INFORMATION FOR SEQ ID NO:15:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: circular ( i i ) MOLECULE TYPE: peptide ( i i i ) HYPOTHETICAL: NO ( i v ) ANTI-SENSE: NO ( x i ) SEQUENCE DESCRIPTION: SEQ ID NO:15:

Xaa Thr Xaa Xaa Xaa Xaa
1               5

( 2 ) INFORMATION FOR SEQ ID NO:16:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: circular ( i i ) MOLECULE TYPE: peptide ( i i i ) HYPOTHETICAL: NO (iv) ANTI-SENSE: NO (xi) SEQUENCE DESCRIPTION: SEQ ID NO:16:

Xaa Ser Xaa Xaa Ser Xaa
1               5

(2) INFORMATION FOR SEQ ID NO:17:

(i) SEQUENCE CHARACTERISTICS:
(A) LENGTH: 6 amino acids
(B) TYPE: amino acid
(C) STRANDEDNESS: unknown
(D) TOPOLOGY: circular (ii) MOLECULE TYPE: peptide (iii) HYPOTHETICAL: NO (iv) ANTI-SENSE: NO (xi) SEQUENCE DESCRIPTION: SEQ ID NO:17:

Xaa Ser Xaa Xaa Thr Xaa
1               5

(2) INFORMATION FOR SEQ ID NO:18:

(i) SEQUENCE CHARACTERISTICS:
(A) LENGTH: 6 amino acids
(B) TYPE: amino acid
(C) STRANDEDNESS: unknown
(D) TOPOLOGY: circular (ii) MOLECULE TYPE: peptide (iii) HYPOTHETICAL: NO (iv) ANTI-SENSE: NO (xi) SEQUENCE DESCRIPTION: SEQ ID NO:18:

Xaa Ser Xaa Xaa Xaa Xaa
1               5

(2) INFORMATION FOR SEQ ID NO:19:

(i) SEQUENCE CHARACTERISTICS:
(A) LENGTH: 6 amino acids
(B) TYPE: amino acid
(C) STRANDEDNESS: unknown
(D) TOPOLOGY: circular (ii) MOLECULE TYPE: peptide (iii) HYPOTHETICAL: NO (iv) ANTI-SENSE: NO (xi) SEQUENCE DESCRIPTION: SEQ ID NO:19:

Xaa Thr Xaa Xaa Ser Xaa
1               5

(2) INFORMATION FOR SEQ ID NO:20:

(i) SEQUENCE CHARACTERISTICS:
(A) LENGTH: 6 amino acids
(B) TYPE: amino acid
(C) STRANDEDNESS: unknown
(D) TOPOLOGY: circular (ii) MOLECULE TYPE: peptide (iii) HYPOTHETICAL: NO ( i v ) ANTI-SENSE: NO ( x i ) SEQUENCE DESCRIPTION: SEQ ID NO:20:

Xaa Thr Xaa Xaa Thr Xaa
1               5

( 2 ) INFORMATION FOR SEQ ID NO:21:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: circular ( i i ) MOLECULE TYPE: peptide ( i i i ) HYPOTHETICAL: NO ( i v ) ANTI-SENSE: NO ( x i ) SEQUENCE DESCRIPTION: SEQ ID NO:21:

Xaa Thr Xaa Xaa Xaa Xaa
1               5

( 2 ) INFORMATION FOR SEQ ID NO:22:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: circular ( i i ) MOLECULE TYPE: peptide ( i i i ) HYPOTHETICAL: NO ( i v ) ANTI-SENSE: NO ( x i ) SEQUENCE DESCRIPTION: SEQ ID NO:22:

Xaa Ser Xaa Xaa Ser Xaa
1               5

( 2 ) INFORMATION FOR SEQ ID NO:23:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: circular ( i i ) MOLECULE TYPE: peptide ( i i i ) HYPOTHETICAL: NO ( i v ) ANTI-SENSE: NO ( x i ) SEQUENCE DESCRIPTION: SEQ ID NO:23:

Xaa Ser Xaa Xaa Thr Xaa
1               5

( 2 ) INFORMATION FOR SEQ ID NO:24:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: circular ( i i ) MOLECULE TYPE: peptide ( i i i ) HYPOTHETICAL: NO (iv) ANTI-SENSE: NO
(xi) SEQUENCE DESCRIPTION: SEQ ID NO:24:
Xaa Ser Xaa Xaa Xaa Xaa
1               5